(12) United States Patent
Worm et al.

(10) Patent No.: US 12,421,552 B2
(45) Date of Patent: Sep. 23, 2025

(54) MICRORNA-134 BIOMARKER

(71) Applicant: Roche Innovation Center Copenhagen A/S, Horsholm (DK)

(72) Inventors: Jesper Worm, Copenhagen (DK); Lukasz Kielpinski, Horsholm (DK)

(73) Assignee: Roche Innovation Center Copenhagen A/S, Horsholm (DK)

(*) Notice: Subject to any disclaimer, the term of this patent is extended or adjusted under 35 U.S.C. 154(b) by 949 days.

(21) Appl. No.: 17/183,273

(22) Filed: Feb. 23, 2021

(65) Prior Publication Data

US 2021/0270845 A1  Sep. 2, 2021

Related U.S. Application Data

(63) Continuation of application No. PCT/EP2019/072312, filed on Aug. 21, 2019.

(30) Foreign Application Priority Data

Aug. 23, 2018 (EP) .................................... 18190523

(51) Int. Cl.
  *C12Q 1/6883* (2018.01)
  *C12N 15/113* (2010.01)

(52) U.S. Cl.
  CPC .......... *C12Q 1/6883* (2013.01); *C12N 15/113* (2013.01); *C12N 2310/11* (2013.01); *C12N 2310/3231* (2013.01); *C12Q 2600/158* (2013.01)

(58) Field of Classification Search
  None
  See application file for complete search history.

(56) References Cited

U.S. PATENT DOCUMENTS

2009/0226905 A1* 9/2009 Joubert ............ G01N 33/57419
                                                                435/7.1
2018/0161357 A1   6/2018 Jackson et al.

FOREIGN PATENT DOCUMENTS

| EP | 1222309 B1 | 12/2005 |
|---|---|---|
| EP | 2841579 A1 | 3/2015 |
| WO | 98/39352 A1 | 9/1998 |
| WO | 99/14226 A2 | 3/1999 |
| WO | 2000/047599 A1 | 8/2000 |
| WO | 00/66604 A2 | 11/2000 |
| WO | 2004/046160 A2 | 6/2004 |
| WO | 2005/013901 A2 | 2/2005 |
| WO | 2007/027775 A2 | 3/2007 |
| WO | 2007/027894 A2 | 3/2007 |
| WO | 2007/090071 A2 | 8/2007 |
| WO | 2007/112754 A2 | 10/2007 |
| WO | 2007/134181 A2 | 11/2007 |
| WO | 2008/150729 A2 | 12/2008 |
| WO | 2008/154401 A2 | 12/2008 |
| WO | 2009/006478 A2 | 1/2009 |
| WO | 2009/043353 A2 | 4/2009 |
| WO | 2009/067647 A1 | 5/2009 |
| WO | 2010/036698 A1 | 4/2010 |
| WO | 2010/077578 A1 | 7/2010 |
| WO | 2011/017521 A2 | 2/2011 |
| WO | 2011/156202 A1 | 12/2011 |
| WO | 2013/045652 A1 | 4/2013 |
| WO | 2013/154798 A1 | 10/2013 |
| WO | 2013/163258 A1 | 10/2013 |
| WO | 2014/076195 A1 | 5/2014 |
| WO | 2015/061536 A1 | 4/2015 |
| WO | 2016/196978 A1 | 12/2016 |
| WO | 2017/035319 A1 | 3/2017 |
| WO | 2018/106566 A1 | 6/2018 |
| WO | 2018/106568 A1 | 6/2018 |

OTHER PUBLICATIONS

Corduan et al. Cellular Haemostasis and Platelets. Feb. 12, 2015. 113: 1046-1059 and Supplementary Material, 29 pages total (Year: 2015).*
Klimczak-Bitner et al. Oncology Letters. 12: 4133-4138 (Year: 2016).*
Campbell et al Molecular Therapy Nucleic Acids. 2022. 28: 514-529 and Supplemental Information, 30 pages total (Year: 2022).*
Polo-Generelo et al Cell Death Discovery. 2024. 10:116 (Year: 2024).*
Vogel et al Nature Review Genet. Mar. 2012. 13(4): 227-232 (Year: 2012).*
Wegler et al NAR Genom Bioinform. Mar. 2020. 2(1): lqz010, 11 pages (Year: 2020).*
Zhang et al Nature. Sep. 18, 2014. 513(7518): 382-387 (Year: 2014).*
Heggard et al. International Journal of Cancer. May 4, 2011. 102. 130: 1378-1386 (Year: 2011).*
Min et al BMC Genomics. 2010. 11:96 (Year: 2010).*
International Search Report and Written Opinion issued in International Application No. PCT/EP2019/072312, dated Oct. 1, 2019, 16 pgs.
Eva M Jimenez-Mateos et al: "Silencing microRNA-134 produces neuro-protective and prolonged seizure-suppressive effects", Nature Medicine, vol. 18, No. 7, Jan. 1, 2012, pp. 1087-1094, XP055049682, ISSN: 1078-8956, DOI: 10.1038/nm.2834, 24 pgs.
F O Akenami et al: "Cerebrospinal fluid plasminogen activator inhibitor-1 in patients with neurological disease", Journal of Clinical Pathology, vol. 50, No. 2, Feb. 1, 1997, pp. 157-160, XP055623008, GB ISSN: 0021-9746, DOI: 10.1136/jcp.50.2.157, 4 pgs.

(Continued)

*Primary Examiner* — Carla J Myers
(74) *Attorney, Agent, or Firm* — Teresa Peterson

(57) ABSTRACT

The invention relates to the field of secondary markers for microRNA activity, and in particular the invention relates to the identification of Serpine1 as a mRNA which is repressed by microRNA-134 in neuronal cells, and the use of Serpine1 mRNA or protein as a biomarker for microRNA-134 modulation, such as a biomarker for antisense oligonucleotide inhibitors of microRNA-134.

10 Claims, 5 Drawing Sheets

Figure 1:
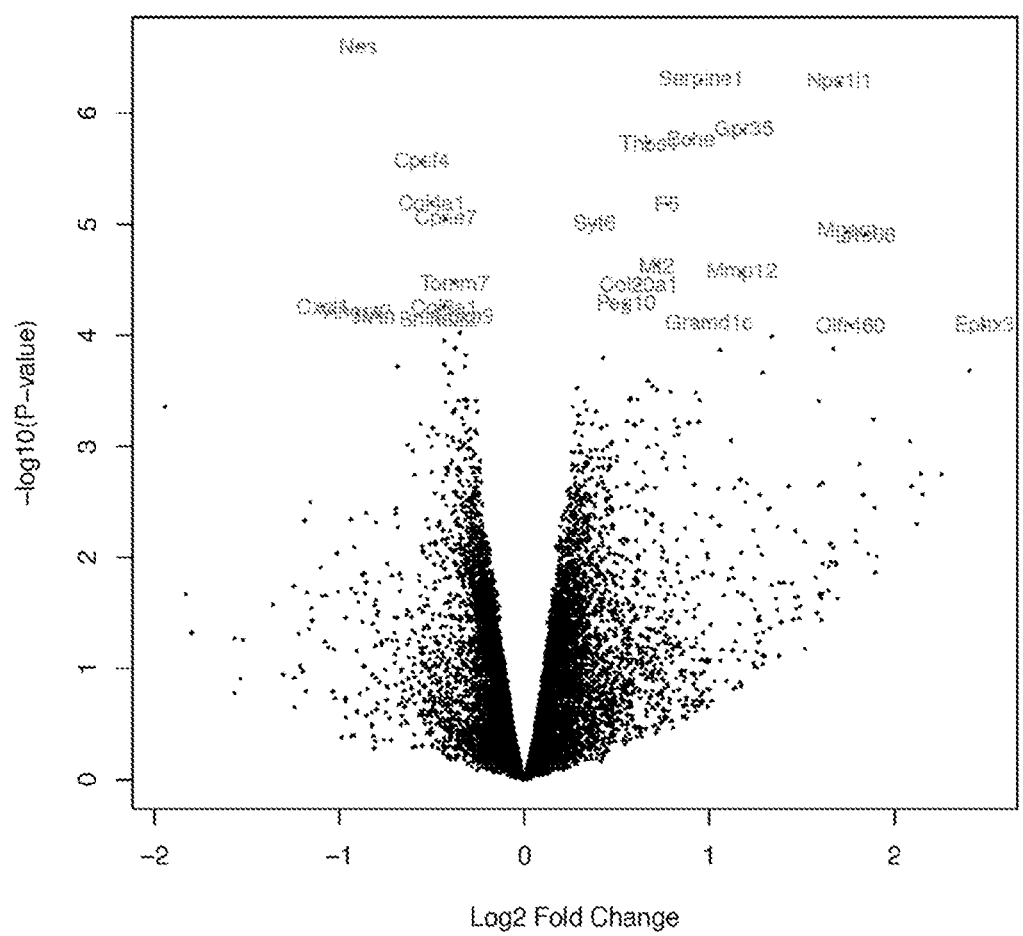

Specification includes a Sequence Listing.

(56) References Cited

OTHER PUBLICATIONS

Bergstrom DE, "Unnatural nucleosides with unusual base pairing properties", Current Protocols in Nucleic Acid Chemistry, 2009, Suppl. 37 1.4.1, 32 pgs.
Davis et al., "Improved targeting of miRNA with antisense oligonucleotides," Nucleic Acids Res., 2006, 34:2294-2304.
Davis et al., Nucleic Acids Res. Jan. 2009; 37(1):70-7.
Ellwanger et al., "The Sufficient Minimal Set of MiRNA Seed Types." Bioinformatics (Oxford, England),2011, 27 (10):1346-50.
Esau C, et al, "miR-122 regulation of lipid metabolism revealed by in vivo antisense targeting", Cell Metab. Feb. 2006, vol. 3(2), pp. 87-98. doi: 10.1016/j.cmet.2006.01.005. PMID: 16459310.
Eva M Jimenez-Mateos, et al, "Antagomirs targeting microRNA-134 increase hippocampal pyramidal neuron spine volume in vivo and protect against pilocarpine-induced status epilepticus", Brain Struct Funct., Jul. 2015, vol. 220(4), pp. 2387-2399. doi: 10.1007/s00429-014-0798-5.
Freier, S.M. et al., The ups and downs of nucleic acid duplex stability: structure-stability studies on chemically-modified DNA:RNA duplexes, Nucleic Acids Research, 1997, vol. 25(22), pp. 4429-4443.
Hansen et al., "Entropy titration. A Calorimetric Method for the Determination of t..G0 (K), t..H0 and t..S0 1," Chemical Communications. 36-38, (1965) (3 pages).
Hirao, I et al., "Natural versus Artificial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.
Holdgate, GA et al., "Measurements of binding thermodynamics in drug discovery," Drug Discovery Today, 2005, vol. 10, No. 22, pp. 1543-1550, 8 pages.
International Preliminary Report on Patentability received for PCT Patent Application No. PCT/EP2019/072312 , mailed on Mar. 4, 2021, 9 pages.
Kim, et al., "HISAT: A Fast Spliced Aligner with Low Memory Requirements", Nature Methods, 2015, 12 (4): 357-60. https://doi.org/10.1038/nmeth.3317.
Krutzfeldt, J., et al., "Silencing of microRNAs in vivo with 'antagomirs'" Nature, vol. 438, No. 7068, Dec. 1, 2005, pp. 685-689.
Law, et al., "Voom: Precision Weights Unlock Linear Model Analysis Tools for RNA-Seq Read Counts", Genome Biology 2004, 15 (2): R29. https://doi.org/10.1186/gb-2014-15-2-r29.
Liao, et al., "The Subread Aligner: Fast, Accurate and Scalable Read Mapping by Seed- and-Vote", Nucleic Acids Research, 2013, 41 (10): e108. https://doi.org/10.1093/nar/gkt214.
McTigue, PM et al., "Sequence-Dependent Thermodynamic Parameters for Locked Nucleic Acid (LNA)-DNA Duplex Formation," Biochemistry, 2004, vol. 43(18), pp. 5388-5405, 18 pages.
Mergny, JL et al., "Analysis of Thermal Melting Curves," Oligonucleotides, 2003, vol. 13(6), pp. 515-537, 23 pages.
Mitsuoka, Y et al., "A bridged nucleic acid, 2',4'-BNACOC: synthesis of fully modified oligonucleotides bearing thymine, 5-methylcytosine, adenine and guanine 2',4'-BNACOC monomers and RNA-selective nucleic-acid recognition," Nucleic Acids Research, 2009, vol. 37, No. 4, pp. 1225-1238, 14 pages.
Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).
Reuter, Jessica S., and David H. Mathews. 2010. "RNAstructure: Software for RNA Secondary Structure Prediction and Analysis." BMC Bioinformatics 11 (March): 129. https://doi.org/10.1186/1471-2105-11-129.
S. Reschke, et al, "Magnetic Excitations and Continuum of a Possibly Field-Induced Quantum Spin Liquid in a-RuCI3", Phys. Rev. Lett. vol. 119, Iss. 22, Dec. 2017, pp. 227202.
Santa Lucia, JJr., "A unified view of polymer, dumbbell, and oligonucleotide DNA nearest-neighborthermodynamics," Proc Nall Acad Sci USA, 1998, 95(4), pp. 1460-1465, 6 pages.
Seth, PP et al., "Synthesis and Biophysical Evaluation of 2',4'-Constrained 2'O-Methoxyethyl and 2',4'-Constrained 2'O-Ethyl Nucleic Acid Analogues," J. Org. Chem., 2010, vol. 75:5, pp. 1569-1581.
Seyed Esmaeil Khoshnam, et al, "Emerging Roles of microRNAs in Ischemic Stroke: As Possible Therapeutic Agents", Journal of Stroke 2017; 19(2):166-187.
Sugimoto, N. et al., Thermodynamic Parameters to Predict Stability of RNA/DNA Hybrid Duplexes, Biochemistry, 1995, vol. 34(35), pp. 11211-11216.
Tsirka S E, et al., showed that excitotoxin-induced neuronal degeneration and seizure are mediated by tissue plasminogen activator. Nature. Sep. 1995. 28; 377(6547):340-4.
Uhlmann; Curr. Opinion in Drug Development, 2000, 3(2), 293-213.
Wan: The Medicinal Chemistry of Therapeutic Oligonucleotides, Journal of Medicinal Chemistry, 2016, 59, 9645-9667, 23 pgs.
Ying Chen, et al, "Isolation and culture of rat and mouse oligodendrocyte precursor cells", Nat Protoc. 2007, vol. 2(5), pp. 1044-1051. doi: 10.1038/nprot.2007.149.
"International Search Report and Written Opinion for PCT/EP2019/072312 Mailed Oct. 1, 2019".
Akenami et al., "Cerebrospinal fluid plasminogen activator inhibitor-1 in patients with neurological disease" J Clin Pathol 50:157-160 ( 1997).
Borstnar et al., "High levels of uPA and PAI-1 predict a good response to anthracyclines" Breast Cancer Research and Treatment 121(3):615-624 (Dec. 29, 2009).
Jimenez-Mateos et al., "Silencing mircroRNA-134 Produces neuroprtoective and prolonged seizure-suppressive effects" Nature Medicine 118(7):1087-1094 (Jul. 2012).
Viala et al., "Prognostic impact of the inclusion of uPA/PAI-1 for adjuvant treatmenet decision-making in ER+/Her2—pN1 early breast cancers" Breast Cancer Resarch and Treatment 165(3):611-621 (Jul. 6, 2017).
Thomas et al., "Rapid Increases in proBDNF after Pilocarpine-Induced Status Epilepticus in Mice Are Associated with Reduced proBDNF Cleavage Machinery" eNeuro 3(1):1-14 (Feb. 2016).

* cited by examiner

MICRORNA-134 BIOMARKER

CROSS REFERENCE TO RELATED APPLICATIONS

This application is a continuation of and claims priority to International Patent Application No. PCT/EP2019/072312, filed Aug. 21, 2019, and entitled "MICRORNA-134 BIOMARKER", which claims priority European Patent Application No. 18190523.3 filed Aug. 23, 2018, the entire disclosures of which are incorporated herein by this reference.

SEQUENCE LISTINGS

This application contains a Sequence Listing which has been submitted electronically and is hereby incorporated by reference in its entirety. Said electronic copy, created on Feb. 25, 2025, is named P34983-US_ST25.txt and is 21,094 bytes in size.

FIELD OF INVENTION

The invention relates to the field of secondary markers for microRNA activity, and in particular the invention relates to the identification of Serpine1 as a mRNA which is repressed by microRNA-134 in neuronal cells, and the use of Serpine1 mRNA or protein as a biomarker for microRNA-134 modulation, such as a biomarker for antisense oligonucleotide inhibitors of microRNA-134. Serpine 1 is also known as Serpin E1; PLANH1; PAI-1.

BACKGROUND microRNAs (miRNAs) are a class of non-coding RNAs that regulate gene-expression post-transcriptionally, and a microRNA may modulate the expression of 100s of mRNAs. Davis et al., Nucleic Acid Research 2009, vol 37, doi:10.1093/nar/gkn904 discusses the importance in evaluation of secondary endpoints as being crucial for interpreting miRNA inhibition studies.

As described in WO2013/045652, microRNA-134 has been indicated as a therapeutic target for the treatment of epilepsy, based upon a strong link between temporal lobe epilepsy (TLE) and increased expression of a miRNA-134 and experimental evidence where LNA antimiRs targeting microRNA-134 suppresses seizure activity and hippocampal activity causes by epilepsy in rodent models (Jimenez-Mateos et al., 2012, Jimenez-Mateos et al., 2015 and Reschke et al., 2017). Remarkably, silencing miR-134 after status epilepticus in rats resulted in 86% reduction in the subsequent occurrence of spontaneous seizures in the perforant pathway stimulation model, a toxin-free model of acquired epilepsy (Reschke et al., 2017). MicroRNA-134 is indicated as a therapeutic agent for the treatment of cerebral ischemic injury (Khoshnam et al., Journal of Stroke 2017; 19(2):166-187). WO2007/112754 discloses LNA antimiRs, including the LNA antimiRs targeting hsa-miR-134 such as 5' TgGtcAAccAgTcAC 3', wherein capital letters are beta-D-oxy-LNA nucleosides, lower case letters are DNA nucleosides, LNA cytosines are 5-methyl cytosine, and all internucleoside linkages are phosphorothioate internucleoside linkages. LNA antimiRs targeting microRNA-134 were used in the examples either as a cholesterol conjugate or as an unconjugated compound. Short fully LNA phosphorothioate oligonucleotides targeting microRNA-134 are disclosed in WO2009043353.

There is therefore interest in the development of therapeutics targeting microRNA-134 for the treatment of epilepsy. This raises a major problem in that whilst microRNA-134 inhibition reduces the severity of the epilepsy condition, very little is known about the underlying mechanism involved, and in particular which mRNAs are modulated by miR-134 or the sub-set of which are involved in disease modulation. This knowledge is required to provide the necessary biomarkers which will allow the identification and development of effective microRNA-134 inhibitor therapeutics, and the monitoring of their effect on microRNA-134 activity in vitro and in vivo. Serpine-1 mRNA has numerous putative microRNA target binding sites in the 3'UTR, including see TargetScanHuman, showing a poorly conserved site annotation for microRNA-134 (targetscan.org).

The present invention is based upon the identification of Serpine1 (PAI-1) as a robust mRNA target for microRNA-134 in primary neurons, and its use as a biomarker for microRNA-134 inhibition.

SUMMARY OF THE INVENTION

The invention provides a method for determining the activity [potency or efficacy, level of inhibition] of a microRNA-134 modulator in a cell, such as a neuronal cell, said method comprising the step of determining the level of a Serpine 1 biomarker in the cell to which a microRNA-134 modulator has been added.

The invention provides a method for identifying a subject suffering from a neurological disorder, such as a neurological disorder associated with seizures, e.g. epilepsy, such as epileptic encephalopathies, or cerebral ischemic injury as likely to benefit from the administration of a therapeutic comprising a microRNA-134 modulator such as an antagonist, said method comprising the steps of
  a) measure the level of a Serpine 1 biomarker in a sample obtained from the subject;
  b) compare to at least one reference level of the Serpine 1 biomarker
  c) to identify whether the subject is likely to benefit from administration of a therapeutic comprising a microRNA-134 modulator, such as an antagonist.

The invention provides a method for determining the efficacy of a microRNA-134 modulator, such as an antagonist, therapeutic in a subject said method comprising the steps of
  a) Measure the level of a Serpine 1 biomarker in a sample obtained from a subject who has previously being administered a microRNA-134 modulator, such as an antagonist, therapeutic
  b) compare to at least one reference level of the Serpine 1 biomarker
  c) to identify the efficacy of the microRNA-134 modulator, such as an antagonist, therapeutic.

The invention provides a method of diagnosing a neurological disorder, such as a neurological disorder associated with seizures, e.g. epilepsy, such as epileptic encephalopathies, or cerebral ischemic injury which is suitable for treatment with a microRNA-134 antagonist therapeutic, said method comprising the steps of
  a. Measure the level of a Serpine 1 biomarker in a sample obtained from the subject;
  b. compare to at least one reference level of the Serpine 1 biomarker
  c. to identify whether the subject is suffering from a neurological disorder, such as a neurological disorder associated with seizures, e.g. epilepsy, such as epileptic encephalopathies, which is suitable for treatment with a microRNA-134 antagonist therapeutic.

The above methods may be in vitro methods.

The invention provides a method of treatment of a neurological disorder, such as a neurological disorder associated with seizures, e.g. epilepsy, such as epileptic encephalopathies, or cerebral ischemic injury, in a subject in need of treatment with a microRNA-134 antagonist therapeutic, said method comprising one of the above methods of the invention (or methods disclosed or claimed herein), followed by the step of administering an effective dose of the microRNA-134 antagonist therapeutic to the subject. In some embodiments the neurological disorder is epilepsy. In some embodiments the neurological disorder is cerebral ischemic injury The invention provides a method of treatment of neurological seizures in a subject in need of treatment with a microRNA-134 antagonist therapeutic, said method comprising one of the above methods of the invention (or methods disclosed or claimed herein), followed by the step of administering an effective dose of the microRNA-134 antagonist therapeutic to the subject.

The invention provides a method of treatment of cerebral ischemic injury in a subject in need of treatment with a microRNA-134 antagonist therapeutic, said method comprising one of the above methods of the invention (or methods disclosed or claimed herein), followed by the step of administering an effective dose of the microRNA-134 antagonist therapeutic to the subject.

The invention provides a method of prophylactic treatment of a neurological disorder, such as a neurological disorder associated with seizures, in a subject in need of treatment with a microRNA-134 antagonist prophylactic therapeutic, said method comprising one of the above methods of the invention (or methods disclosed or claimed herein), followed by the step of administering an effective dose of the microRNA-134 antagonist therapeutic to the subject in need of prophylactic treatment. In some embodiments the neurological disorder is epilepsy. In some embodiments the neurological disorder is cerebral ischemic injury.

The invention provides a method of prophylactic treatment of neurological seizures in a subject in need of treatment with a microRNA-134 antagonist prophylactic therapeutic, said method comprising one of the above methods of the invention (or methods disclosed or claimed herein), followed by the step of administering an effective dose of the microRNA-134 antagonist therapeutic to the subject in need of prophylactic treatment.

The invention provides for the in vitro use of a Serpine 1 biomarker assay for the measurement of microRNA-134 modulation, such as microRNA-134 inhibition.

The invention provides for the in vitro use of a Serpine 1 biomarker assay, as a companion diagnostic for a microRNA-134 modulator, such as antagonist, therapeutic, for example a microRNA-134 antagonist therapeutic for use in the treatment of a neurological disorder, such as a neurological disorder associated with seizures, e.g. epilepsy, such as epileptic encephalopathies, or cerebral ischemic injury.

The invention provides for the in vitro use of a Serpine 1 biomarker for determining the likely response of a subject suffering from a neurological disorder, such as a neurological disorder associated with seizures, e.g. epilepsy, such as epileptic encephalopathies, or cerebral ischemic injury, to a therapeutic agent comprising a microRNA-134 modulator.

The invention provides for the in vitro use of a Serpine 1 biomarker assay, as a companion diagnostic for a microRNA-134 modulator, such as antagonist, therapeutic, for example a microRNA-134 antagonist therapeutic for use in the treatment of neurological seizures and/or cerebral ischemic injury.

The invention provides for the in vitro use of a Serpine 1 biomarker for determining the likely response of a subject suffering from a neurological seizures, e.g. epilepsy, such as epileptic encephalopathies, or seizures associated with cerebral ischemic injury to a therapeutic agent comprising a microRNA-134 modulator.

The invention provides for a method for determining the activity of an exogenously administered microRNA-134 modulator in a cell, said method comprising the step of determining the level of Serpine 1 mRNA, Serpine 1 protein or Serpine 1 activity in a cell to which a microRNA-134 modulator has been administered. It will be understood that in some embodiments the activity is measured in an extract obtained from the cell.

The invention provides for the use of a Serpine 1 mRNA assay, a Serpine 1 protein assay or Serpine 1 activity assay as a biomarker for microRNA-134 modulation, such as microRNA-134 inhibition.

The invention provides for the use of Serpine 1 mRNA, Serpine 1 protein or Serpine 1 activity, as a companion diagnostic for a microRNA-134 antagonist therapeutic, such as a microRNA-134 antagonist therapeutic for use in the treatment of a neurological disorder, such as a neurological disorder associated with siezures, such as epilepsy or cerebral ischemic injury.

The invention provides for the use of Serpine 1 mRNA, Serpine 1 protein or Serpine 1 activity, as a companion diagnostic for a microRNA-134 antagonist therapeutic, such as a microRNA-134 antagonist therapeutic for use in the treatment of neurological seizures.

The invention provides for the use of a Serpine 1 antibody for the determination of Serpine 1 protein levels in a sample obtained from a subject who is undergoing treatment with a microRNA-134 modulator, such as a microRNA-134 antagonist, or is being assessed for suitability of treatment with a microRNA-134 modulator, such as a microRNA-134 antagonist.

The invention provides for the use of a Serpine 1 mRNA detection probe for the determination of Serpine 1 mRNA levels in a sample obtained from a subject who is undergoing treatment with a microRNA-134 modulator, microRNA-134 antagonist, or is being assessed for suitability of treatment with a microRNA-134 modulator, such as a microRNA-134 antagonist.

The invention provides for the use of a Serpine 1 mRNA RT-PCR assay for the determination of Serpine 1 mRNA levels in a sample obtained from a subject who is undergoing treatment with a microRNA-134 modulator, microRNA-134 antagonist or is being assessed for suitability of treatment with a microRNA-134 modulator, such as a microRNA-134 antagonist.

The invention provides for the use of a Serpine 1 activity assay for the determination of Serpine 1 activity levels in a sample obtained from a subject who is undergoing treatment with a microRNA-134 modulator, microRNA-134 antagonist or is being assessed for suitability of treatment with a microRNA-134 modulator, such as a microRNA-134 antagonist.

The invention provides for the use of a tissue plasminogen activator (tPA) assay for the determination of Serpine 1 activity levels in a sample obtained from a subject who is undergoing treatment with a microRNA-134 modulator, suhc as a microRNA-134 antagonist or is being assessed for suitability of treatment with an microRNA-134 modulator, such as a microRNA-134 antagonist.

The invention provides for the use of a Serpine 1 biomarker for determining the likely response of a subject to a therapeutic agent comprising a microRNA-134 modulator, wherein the biomarker is an altered level of Serpine 1 mRNA, protein or activity in a biological sample obtained from the subject, as compared to the level obtained from a reference sample, such as a sample from a healthy subject, a sample for a diseased subject or one or more previous samples obtained from the subject.

The invention provides for the use of a Serpine 1 biomarker for patient monitoring of a subject receiving treatment with a microRNA-134 antagonist e.g. for the treatment of a neurological disorder, such as a neurological disorder associated with seizures, such as epilepsy or cerebral ischemic injury, such as to monitor the effectiveness of the microRNA-134 antagonist.

The invention provides for the use of a Serpine 1 biomarker for patient monitoring of a subject receiving treatment with a microRNA-134 antagonist for the treatment of a neurological seizures.

In some embodiments the neurological disorder is epileptic encephalopathies.

FIGURE LEGENDS

FIG. 1. RNA sequencing analysis identifies genes with significantly different expression level after 6 days treatment of primary mouse cortical neurons with 0.1 µM miR-134 AntimiR. Volcano plot showing differences in gene expression between control Mock treated primary cortical neurons and primary cortical neurons treated with 0.1 µM miR-134 LNA AntimiR (upregulated genes to the right and downregulated genes to the left). Experiment and data analysis are described in Example 1. Each point corresponds to a gene. Genes, whose expression level differs between those two conditions with multiple testing adjusted P-value <0.05 are labeled with gene names.

Figure 2A:
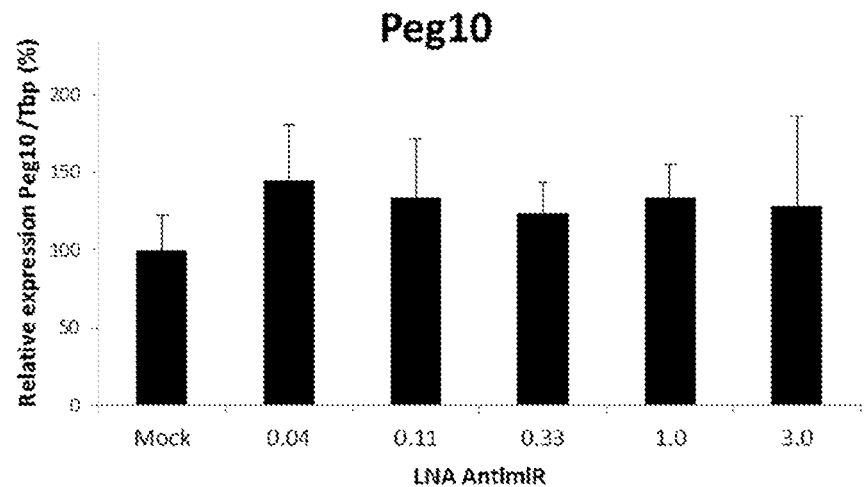
Figure 2B:
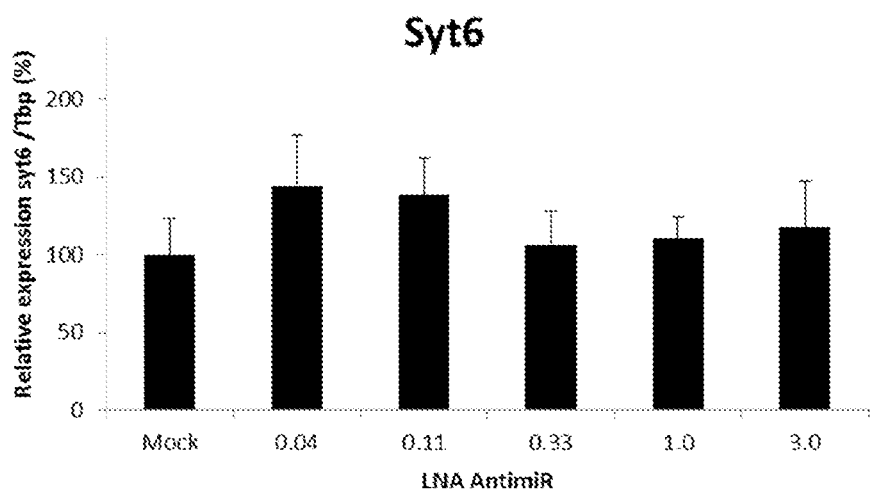
Figure 2C:
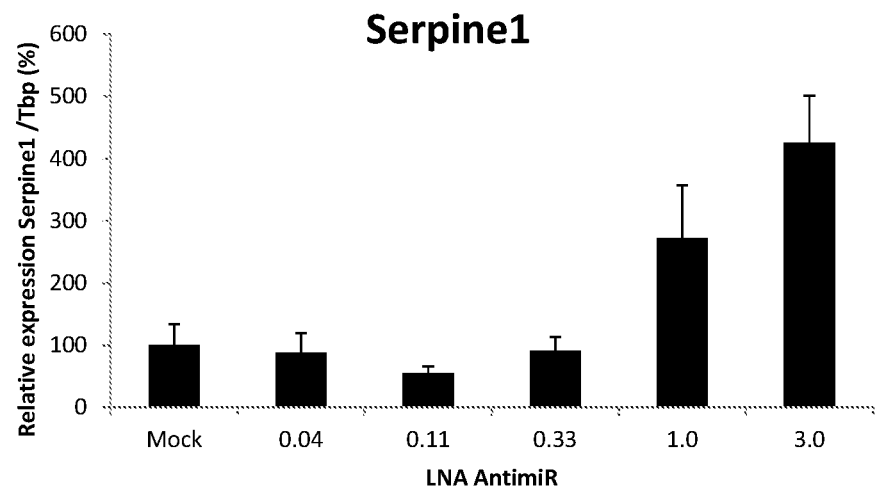

FIG. 2. Validation of candidate miR-134 targets identified by RNA sequencing. ddPCR for the target genes Syt6 (FIG. 2A), Peg10 (FIG. 2B) and Serpine 1 (FIG. 2C) were performed on RNA isolated from primary cortical neurons treated for 5 days with miR-134 inhibitor LNA antimiR. Gpr36 was below detection level (data not shown). Serpine1 was significantly upregulated in a dose-dependent manner by the LNA Antimir inhibitor of miR-134. Experiment described in Example 2.

Figure 3:
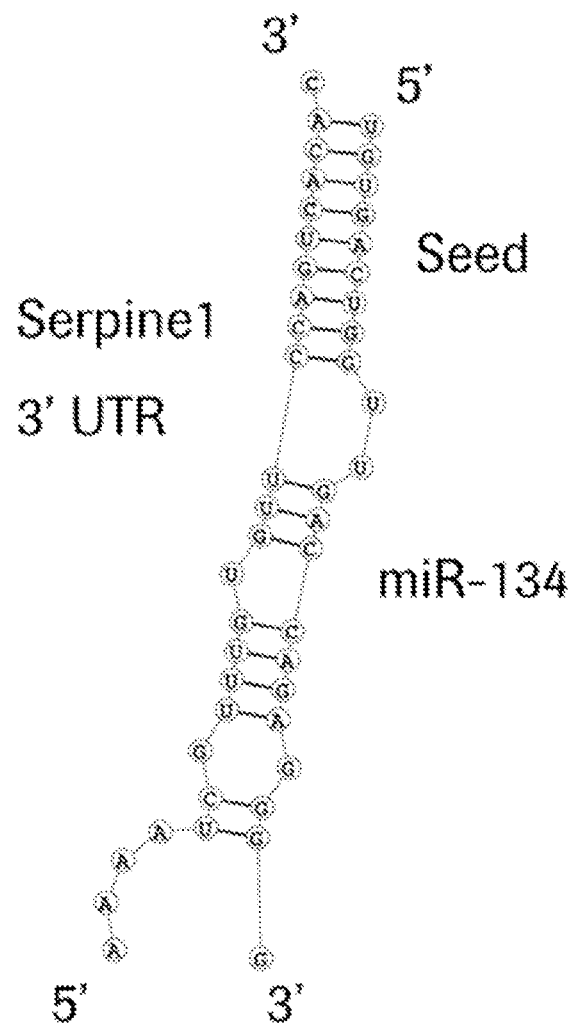

FIG. 3. Illustration of a hybridization of the miR-134 seed sequence to a region of mouse 3' UTR of Serpine1. The seed miR-134 corresponds to SEQ ID NO: 01. "Serpine1 3'-UTR" corresponds to SEQ ID NO: 10.

Figure 4:
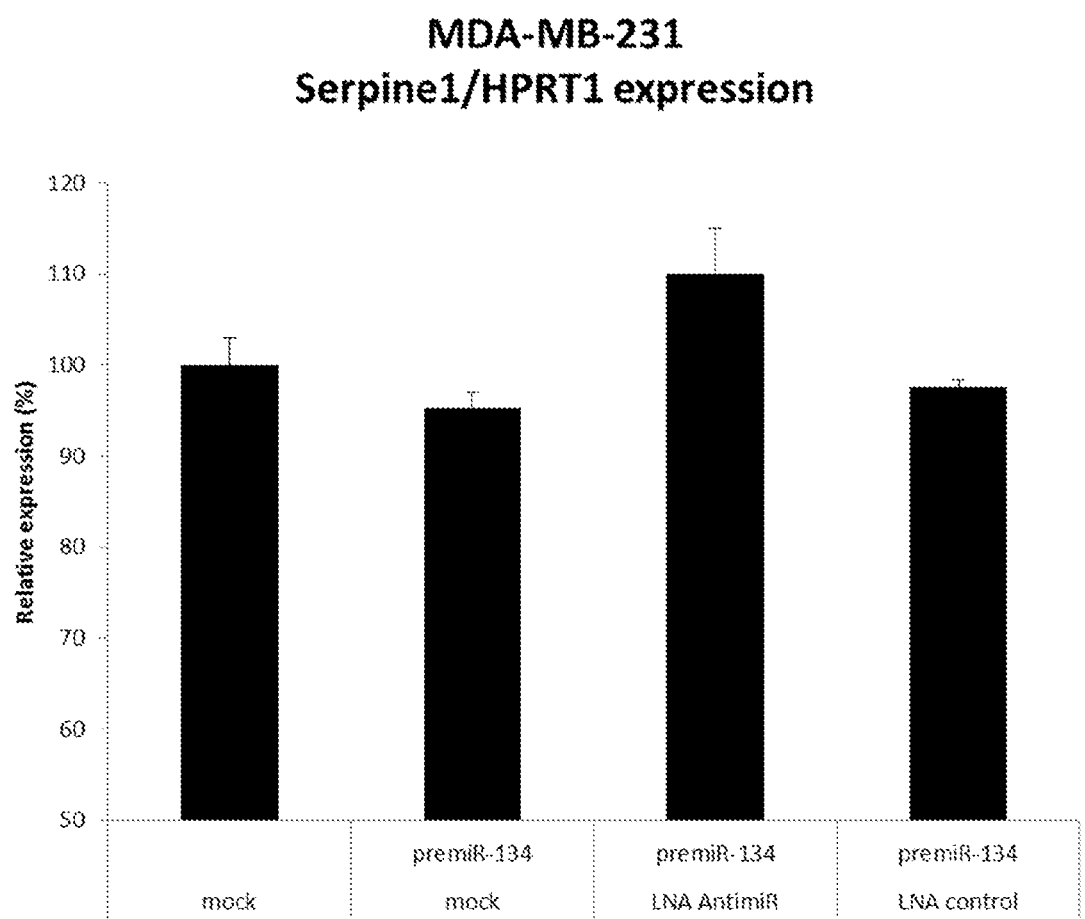

FIG. 4. Serpine1 mRNA expression in human MDA-MB-231 cells (n=3) 48 h after transfection of premiR-134 and mock (PBS), LNA antimiR or LNA control. LNA antimiR treatment both significantly upregulated Serpine1 relative to mock (PBS) treated cells (p<0.01, Students T-test) and to LNA control treated cells. (p<0.05, Students T-test)

DETAILED DESCRIPTION OF THE INVENTION

Method A: The invention provides for a method for determining the activity, such as the potency or efficacy or level of inhibition, of a microRNA-134 modulator in a cell, such as a neuronal cell, said method comprising the step of determining the level of a Serpine 1 biomarker in the cell to which a microRNA-134 modulator has been added. The method may be an in vitro method.

The cell may be a primary cell, for example a primary neuronal cell.

Activity may for example refer to the potency, efficacy or level of inhibition of microRNA-134, and may be compared to one or more reference samples or values.

Method B: The invention provides for a method for identifying a subject suffering from a neurological disorder as likely to benefit from the administration of a therapeutic comprising a microRNA-134 antagonist, said method comprising the steps of
   a) measure the level of a Serpine 1 biomarker in a sample obtained from the subject; compare to at least one reference level of the Serpine 1 biomarker
   b) to identify whether the subject is likely to benefit from administration of a therapeutic comprising a microRNA-134 modulator, such as an antagonist.

Method C: The invention provides for a method for determining the efficacy of a microRNA-134 modulator, such as an antagonist, therapeutic in a subject said method comprising the steps of
   a) Measure the level of a Serpine 1 biomarker in a sample obtained from a subject who has previously being administered a microRNA-134 modulator, such as an antagonist, therapeutic
   b) compare to at least one reference level of the Serpine 1 biomarker to identify the efficacy of the microRNA-134 modulator, such as an antagonist, therapeutic.

Method D: The invention provides for a method of diagnosing a neurological disorder (such as a seizure associated neurological disorder, such as epilepsy or cerebral ischemic injury. ), which is suitable for treatment with a microRNA-134 antagonist therapeutic, said method comprising the steps of
   a) Measure the level of a Serpine 1 biomarker in a sample obtained from the subject;
   b) compare to at least one reference level of the Serpine 1 biomarker to identify whether the subject is suffering from a neurological disorder which is suitable for treatment with a microRNA-134 antagonist therapeutic Method E: The invention provides for a method of treatment of a neurological disorder such as epilepsy in a subject in need of treatment with a microRNA-134 antagonist therapeutic, said method comprising the methods according to any one of claims 1-4, followed by the step of administering an effective dose of the microRNA-134 antagonist therapeutic to the subject. The treatment may be prophylactic—i.e. preventative treatment of a subject who is at risk of developing a neurological disorder, such as a seizure associated neurological disorder, such as epilepsy or seizures associated with cerebral ischemic injury. The treatment may be therapeutic—i.e. treatment after the symptoms of the disease have been diagnosed (such as seizures, such as epilepsy).

The neurological disorder may be a neurological disorder which is associated with a risk or is characterized by the seizures, such as epilepsy or cerebral ischemic injury.

The reference level may, for example be either
   a. a level of Serpine 1 biomarker associated with a disease,
   b. a normal level of Serpine 1 biomarker
   c. both a) and b)

In some embodiments, a reduced level of the Serpine-1 biomarker, such as Serpine-1 mRNA, protein, or Serpine-1 activity is indicative or an elevated microRNA-134 activity, or a higher is indicative of a reduced microRNA-134 activity. (Increase in direct biomarker of Serpine-1 is correlated to microRNA inhibition and Serpine-1 de-repression).

Indirect Serpine-1 biomarkers: As Serpine 1 (PAI-1) is an inhibitor of tPA-1, and elevation in PAI-1 due to microRNA-134 inhibition will result in a decrease in tPA activity, and a reduced conversion of plasminogen to plasmin (clotting).

The invention provides for the use of a Serpine 1 biomarker assay for the measurement of microRNA-134 modulation, such as microRNA-134 inhibition. The use may, for example be an in vitro use.

The invention provides for the use of a Serpine 1 biomarker assay, as a companion diagnostic for a microRNA-134 modulator, such as antagonist, therapeutic, for example a microRNA-134 antagonist therapeutic for use in the treatment of a neurological disorder such as a neurological disorder associated with seizures, such as epilepsy or cerebral ischemic injury. The use may, for example be an in vitro use.

The invention provides for the use of a Serpine 1 biomarker for determining the likely response of a subject suffering from a neurological disorder to a therapeutic agent comprising a microRNA-134 modulator. The use may, for example be an in vitro use.

The Serpine 1 biomarker assay may be selected from the group consisting of
a. Measurement of the Serpine 1 mRNA
b. Measurement of the Serpine 1 protein
c. Measurement of the Serpine 1 activity
d. Measurement of tissue plasminogen activator (tPA) activity
e. Measurement of plasminogen to plasmin conversion, or blood clotting.

a), b) and c) are direct assays of Serpine-1 biomarker, where as d. and e. are indirect Serpine-1 biomarkers. In some embodiments the Serpine 1 biomarker assay is a direct Serpine-1 biomarker assay. In some embodiments the Serpine 1 biomarker assay is an indirect Serpine-1 biomarker assay.

In some embodiments the subject is either suffering from a disease or disorder associated with microRNA-134, such as a neurological disorder, in particular seizure associated neurological disorders such as a epilepsy or cerebral ischemic injury, or is likely to develop a disease or disorder associated with microRNA-134, such as a neurological disorder, in particular seizure associated neurological disorders such as a epilepsy or cerebral ischemic injury.

In some embodiments, the subject has previously undergone tPA (tissue plasminogen activator) treatment, e.g. for thrombosis.

In some embodiments, the Serpine 1 biomarker is assayed in a sample obtained from the subject, selected from the group consisting of a cerebrospinal fluid sample, a blood sample, or a blood plasma sample.

In some embodiments, the Serpine 1 biomarker is assayed in a cerebrospinal sample obtained from the subject.

In some embodiments the microRNA-134 modulator is an antisense oligonucleotide inhibitor of microRNA-134, which comprises at least 7 contiguous nucleotides which are complementary to, such as fully complementary to microRNA-134, such as hsa-miR-134, such as SEQ ID NO: 1 or 2:

In some embodiments, the microRNA-134 antagonist is a LNA antisense oligonucleotide, such as a LNA phosphorothioate antisense oligonucleotide.

microRNA-134 (Also Referred to as miR-134)

MicroRNA-134 was first reported as a tissue specific microRNA in Lagos-Quintana et al., Curr Biol. 12:735-739 (2002). The mouse miR-134 pre-miRNA, mmu-mir-134 M10000160 has the sequence: AGGGUGUGUGACUG-GUUGACCAGAGGGGCGUGCACUCUGUUCACCCU-GUGGGCCA CCUAGUCACCAACCCU (SEQ ID NO: 9)

The mouse mature mmu-miR-134-5p MIMAT0000146 has the sequence UGUGACUGGUUGACCAGAGGGG (SEQ ID NO: 1)

The human microRNA-134 (Gene ID: 406924) is encoded on chromosome 14, location NC_000014.9 (101054687 . . . 101054759)—Annotation release 109 (Assembly GRCh38.p12-GCF_000001405.38).

hsa-mir-134 M10000474 pre-mRNA sequence (stem-loop): CAGGGUGUGUGACUGGUUGACCAGAGGGG-CAUGCACUGUGUUCACCCUGUGGGCC ACCUAGU-CACCAACCCUC (SEQ ID NO: 2)

hsa-miR-134-5p mature microRNA sequence MIMAT0000447: UGUGACUGGUUGACCAGAGGGG (SEQ ID NO: 1)

The microRNA-134 seed sequence in human and mouse is GUGACU or GUGACUG. miR-134, particularly the mature microRNA-134 sequence is highly conserved, between mouse, primates and humans and mammals in general.

microRNA-134 Modulator

A microRNA-134 modulator is a compound which modulates the level of microRNA-134 activity in a cell. The microRNA-134 modulator, such as microRNA-134 inhibitor is advantageously a man-made compound, a synthetically produced compound, an isolated compound or a purified compound. In some embodiments the microRNA-134 modulator is or comprises a synthetically synthesized oligonucleotide. The synthetically synthesized oligonucleotide advantageously comprises at least one modified nucleoside or at least one modified internucleoside linkage.

In some embodiments, the microRNA-134 modulator is or comprises a synthetic microRNAs—i.e. a synthetic oligonucleotide which mimics the activity of microRNA-134 when administered to a cell.

In some embodiments, the microRNA-134 modulator is or comprises a synthetic inhibitor or microRNA-134, such as an antisense oligonucleotide targeting microRNA-134.

In some embodiments Serpine-1 biomarker may be used to identify microRNA modulators—microRNA-134 mimics will enhance the microRNA-134 repression of Serpine-1, whereas microRNA-134 antagonists will result in de-repression of Serpine-1.

In some embodiments, the miR-134 modulators for use in the present invention are microRNA-134 inhibiting antisense oligonucleotides, such as LNA antimiRs, which comprise a contiguous nucleotide sequence of at least 7 nucleotides which are fully complementary to a microRNA-134 target sequence, such as SEQ ID NO: 1 or 2. Suitable, the miR-134 inhibiting antisense oligonucleotides are pharmaceutically active. In the context of this invention pharmaceutically active compounds denotes compounds that may have the potential, based on pre-clinical data such as in vitro (e.g. cell based assays) or in vivo (e.g. animal data such as mouse data), to provide a benefit to a subject.

microRNA-134 Antagonist

One type of modulation, referred to herein as microRNA-134 antagonists/antagonism, is the ability of a compounds to inhibit, down-regulate, reduce, suppress, remove, stop, block, prevent, lessen, lower, avoid or terminate expression of microRNA-134 e.g. by degradation of microRNA-134 RNA or by inactivation of microRNA-134 activity in the cell, e.g. by binding to (e.g. hybridizing to) the microRNA-134 RNA target, thereby preventing the interaction of the microRNA-134 RNA with mRNAs in the cell. High affinity modified oligonucleotides targeting microRNAs, such as LNA antimiRs, are thought to form highly stable duplexes with their target microRNAs, thereby effectively titrating out the microRNA activity.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides.

Antisense Oligonucleotides

The term "Antisense oligonucleotide" as used herein is defined as oligonucleotides capable of modulating expression of a target gene by hybridizing to a target nucleic acid, in particular to a contiguous sequence on a target nucleic acid. LNA antimiRs are an exemplary antisense oligonucleotide which are used to inhibit microRNAs in vitro and in vivo.

Antisense oligonucleotides for use in the present invention comprise at least 7 contiguous nucleotides which are fully complementary to a microRNA-134 target sequence, such as SEQ ID NO: 1 or 2. Advantageously, the antisense oligonucleotide of the invention is complementary to the microRNA-134 seed sequence. The microRNA-134 seed sequence in humans is GUGACU or GUGACUG. In some embodiments, the antisense oligonucleotide referred to in the present invention comprises the complement sequence of the microRNA seed sequence, such as the sequence of nucleotides, AGTCAC or AGUCAC or CAGTCAC or CAGUCAC. Please note that for Watson Crick base paring T and U may be used interchangeably. Advantageously the complement of the seed sequence within the antisense oligonucleotide comprises at least 1 high affinity modified nucleosides, such as at least 1 LNA or at least 1 2'O-MOE nucleoside. In some embodiments, the complement of the seed sequence within the antisense oligonucleotide comprises at least 2 high affinity modified nucleosides, such as at least 2 LNA or at least 2 2'O-MOE nucleosides. In some embodiments, the complement of the seed sequence within the antisense oligonucleotide comprises at least 3 high affinity modified nucleosides, such as at least 3 LNA or at least 3 2'O-MOE nucleosides.

In some embodiments the antisense oligonucleotide referred to in the present invention comprise a contiguous nucleotide sequence of 7-26 nucleotides in length, such as 7-12 nucleotides in length, e.g. 8, 9, 10, 11 or 12 nucleotides in length, or 12-26 nucleotides in length, such as 12, 13, 14, 15, 16, 17, 18, 19, 20, 21, 22, 23, 24, 25 or 26 contiguous nucleotides in length.

Advantageously, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

LNA-AntimiRs

LNA-antimiRs are antisense oligonucleotides which comprise a contiguous nucleotide sequence complementary to the target microRNA, e.g. hsa-miR-134, which comprise at least one LNA nucleoside. LNA-antimiRs are described in WO2007/112754 and WO2009043353, hereby incorporated by reference. See also the mixmer and totalmer compounds described herein.

Other LNA-antimiR designs are disclosed in WO2007/027775, WO07027894, WO2015/061536, WO2017035319, WO2018/106566, EP2841579 and WO18106568. It is preferable that the antisense oligonucleotide microRNA-134 antagonist comprise the sequence 5' agtcac 3' or 5' cagtcac 3'—these sequences are or comprise the complement of the hsa-miR-134 seed region. In some embodiments, the antisense oligonucleotide microRNA-134 antagonist referred to herein comprise a sequence 5' agtcac 3', wherein at least 1, such as 2, 3, 4, 5 or 6 of the nucleosides in the 5' agtcac 3' are LNA nucleosides. One exemplary LNA-antimiR is the antisense oligonucleotide, 5' TgGtcAAccAgTcAC 3' (SEQ ID NO: 8), wherein capital letters are beta-D-oxy-LNA nucleosides, lower case letters are DNA nucleosides, LNA cytosines are 5-methyl cytosine, and all internucleoside linkages are phosphorothioate internucleoside linkages.

In advantageous embodiments, the modulator comprises an antisense LNA oligonucleotide. In one specially preferred embodiment, the modulator comprises an oligonucleotide which is between 7 and 25 nucleotides long and comprises at least one LNA. In some embodiments, the microRNA modulator comprises an oligonucleotide which is between 7 and 25 nucleotides long and comprises at least one LNA, and further comprises at least one other affinity increasing nucleotide analogue. In some embodiments, the oligonucleotide of the invention comprise phosphorothioate linkages.

In some embodiments the anti-miR-134 oligonucleotide is a LNA antimiR (see WO2007/112754 for example). LNA antimiRs are antisense oligonucleotides complementary to the mature microRNA target which comprise LNA nucleosides, and may further comprise phosphorothioate internucleotide linkages. LNA antimiRs may further comprise other nucleotides such as DNA and/or 2'-O-methoxyethyl (MOE) nucleosides (See EP1931780 for example). It is advantageous for targeting mature microRNAs that antimiR-134 oligonucleotides do not recruit RNaseH1, and as such it is advantageous that the anti-miR-134 oligonucleotide, such as the LNA antimiRs do not contain regions of 4 or more contiguous DNA nucleosides.

Anti-microRNA LNA phosphorothioates may be ordered from Qiagen (qiagen.com).

Compound C (Exiqon antagomir) used in the experiments described herein can be obtained from this source.

Advantageously anti-miR-134 oligonucleotides which target the mature microRNA-134 target nucleic acid comprises the complement to the microRNA-134 seed region (nucleotides 2-7 from the 5' end of hsa-miR-134). In some embodiments the anti-miR 134 oligonucleotide comprises at least 1, such as at least 2 or at least 3 LNA nucleotides which are located in positions which are complementary to the microRNA-134 seed region (e.g the anti miR-134 oligonucleotide comprises the sequence CAGTCAC or AGTCAC).

LNA antimiRs may be fully phosphorothioate or may be partially phosphorothioate. For systemic administration a high proportion of fully phosphorothioate antisense oligonucleotides may be preferred, however for local administration to the CNS, it may be desirable to use partial phosphorothioates.

In some embodiments the anti-miR-134 oligonucleotide is 7-10 contiguous LNA nucleotides in length (also refered to as Tiny LNAs, see Obad et al., Nat Genet. 2011 Mar. 20; 43(4):371-8, and WO2009043353 and comprises the complement of the microRNA-134 seed region. Examples of TINY LNA inhibitors of hsa-miR-134 include: ACCAGT-CAC, CCAGTCAC & CAGTCAC, wherein each nucleotide is a LNA nucleoside such as beta-D-oxy LNA, and all internucleoside linkages are phosphorothioate. Use of partial phosphorothioates may also be used, for example the internucleoside linkages between the terminal nucleotises may be phosphorothioate, and the remaining internucleoside linkages may be phosphodiester.

In an embodiment, the pharmaceutical composition comprise an anti-miR-134 oligomer having the sequence: 5'-TgGtcAAccAgTcAC-3' (SEQ ID NO: 8) also referred to as compound A herein, wherein Capital letters indicate beta-D-oxy LNA, lower case DNA and LNA C is 5 methylC and wherein such compound as a fully phosphorothioate backbone. This oligomer can be prepared as described in WO 2007/112754. Other oligomers of WO 2007/112754 can be used according to the invention, the content of which is hereby incorporated by reference.

In some embodiments, the microRNA-134 inhibitor is an LNA antisense oligomer comprising or consisting of any one of the sequences listed in Table 1.

Table 1. The following specific sequences or compounds, which may be used in the methods of the present invention, such as in the treatment of a disease, such as a disease where expression/over-expression of miR-134 are indicated such as those diseases illustrated in table 1. The compounds are preferably fully phosphorothioate and each nucleotide is a LNA nucleotide, such as beta-D-oxy LNA. LNA cytosine may be 5'methyl cytosine. Equivalent antimiRs can be designed by matching the –2 to –8/–9 or –10 positions (for 7, 8 or 9mers) of mature microRNAs (counting from the terminal 5' nucleotide of the microRNA (i.e. at the –1 position).

TABLE 1

| Sequence | SEQ ID NO: |
|---|---|
| CCCCTCTGGTCAACCAGTCACA | 4 |
| CCTCTGGTCAACCAGTCAC | 5 |
| 5'-TgGtcAAccAgTcAC-3'* | 6 |

*wherein Capital letters indicate beta-D-oxy LNA, lower case DNA and LNA C is 5 methylC and wherein such compound as a fully phosphorothioate backbone.

Numerous other chemistries and designs of anti-microRNA oligonucleotides are known in the art.

For microRNA inhibition in vivo numerous chemistries and designs have been used in the art, including non RNaseH recruiting antisense oligonucleotide targeting mature microRNA targets, e.g.:

Full 2'-O-methoxyethyl phosphorothioates as reported in WO2005013901, Esau et al., Cell Metab. 2006 February; 3(2):87-98 and Davis et al, Nucleic Acids Res. 2006 May 11; 34(8):2294-304.

2'-O-methoxyethyl/2' fluoro mixmer phosphorothioates—See Davis et al., Nucleic Acids Res. 2009 January; 37(1): 70-7.

2'-O-methyl AntagomiRs—fully 2'-O-methyl modified full complements of mature microRNAs, where the 5' and 3' regions are phosphorothioate with an internal region of phosphodiester, incorporating a cholesterol conjugate (Krutzfeldt et al., Nature. 2005 Dec. 1; 438(7068):685-9)

For targeting pre-microRNA targets, RNaseH recruiting designs are reported to be functional, see WO2005013901 which discloses 2'-O-methoxyethy gapmers targeting pre-miRNA target sequences.

microRNA-134 Antagonist Therapeutic

A microRNA-134 antagonist therapeutic is a microRNA-134 inhibitor which has been discovered, developed or has market approval for, or is marketed for the inhibition of microRNA-134 for the prevention of, or for the treatment of a microRNA-134 related disease or disorder, such as a neurological disorder associated with seizures such as epilepsy or cerebral ischemic injury.

Serpine 1 Biomarker

A Serpine 1 biomarker is a direct or indirect biomarker of Serpine 1 expression or activity in a cell or sample.

Direct biomarkers of Serpine 1 expression include:

The measurement of Serpine 1 mRNA, e.g. using a hybridasation based assay (e.g. northern blot, RT-PCR, probe hybridization, microarray analysis, RNA protection assays, or RNA sequencing).

A Serpine1 pre-mRNA is encoded at human Chromosome 7:101,127,089-101,139,266 forward strand (GRCh38: CM000669.2), as provided herein by example as SEQ ID NO: 3 (SERPINE1-201).

The measurement of Serpine 1 protein levels, e.g. using a Serpine 1 specific antibody. Numerous Serpine 1 specific antibodies are commercially available. Serpine-1 antibody assays may be used to measure Serpine 1 protein levels using e.g. an Elisa assays, which are also commercially available e.g. Human PAI1 ELISA Kit (SERPINE1) (ab184863) available from abcam. An example of the human Serpine1 protein sequence is provided as SEQ ID NO: 7.

Serpine 1 is a regulator of tissue plasminogen activator (tPA). tPA is a serine protease which converts plasminogen to plasmin, the major enzyme responsible for clot breakdown. Indirect biomarkers of Serpine 1 expression include assays for tPA activity, which are commercially available, e.g. from AnaSpec—SensoLyte® AMC tPA Activity Assay Kit *Fluorimetric*. Elisa assays for tPA are also commercially available. Furthermore, as Serpine-1 inhibits tPA, and tPA converts plasminogen to plasmin, the conversion of plasminogen to plasmin, such as a clotting assay, may also be used as a Serpine-1 biomarker.

Reference Levels

In the methods of use of the invention, the level of Serpine-1 biomarker may be compared to at least one reference level. A reference level may, for example be the a level of Serpine 1 biomarker associated with a disease, and/or a normal level of Serpine 1 biomarker. The levels of Serpine-1 biomarker may be determined for example, from a population of subjects, e.g. a population of subjects who have been diagnosed with the disease, and/or a population of subjects who are considered to not have the disease.

In addition or alternatively, the Serpine-1 reference may be a historic Serpine-1 biomarker level from the subject, e.g. for use in patient/subject monitoring for subjects who have been administered a microRNA-134 antagonist therapeutic. The present invention may therefore be used to monitor patients for effective microRNA-134 inhibition, and thereby to optimize the dosage regimen for the individual subject/patient.

The Subject

The subject may be a mammal, such as a rodent, e.g. a rat or a mouse, or a primate, such as a monkey (e.g. cynomolgus monkey).

The subject may be a non-human animal model for a microRNA-134 related disease. In some embodiments the animal model is a mouse model based on chemical (Kainic acid) induced seizures.

The subject may be a human being, such as a human being who is in need of treatment with a microRNA-134 antagonist therapeutic, or who is undergoing treatment with a microRNA-134 antagonist therapeutic.

The subject may be a human being who suffers from a neurological disorder associated with (e.g. characterized by, or at risk of) seizures The subject may be a human being who suffers from a cerebral ischemic injury.

The subject may be a human being who has been diagnosed with either having a microRNA-134 related disease or disorder, such as epilepsy, or has been diagnosed at risk of developing a microRNA-134 related disease or disorder, such as epilepsy.

The subject may have previously undergone tPA (tissue plasminogen activator) treatment, e.g. for thrombosis (such subjects may have be at risk of developing epilepsy). In such an instance, the method or use of the invention may be used diagnostically—i.e. to identify those subjects who have an elevated risk of developing seizures (such as epilepsy), and/or therapeutically—i.e. to prevent or treat seizures (such as) epilepsy. The seizures may be associated with a neurological disorder, such as a cerebral ischemic injury.

MicroRNA-134 Related Disease or Disorders microRNA-134 is a brain specific miRNA which is implicated in neuronal microstructures, and microRNA-134 overexpression has been linked with reduce spinal volume, reduced dendritic length and abrogation of long-term potentiation. microRNA-134 is therefore an interesting target for treatment of various neurological disorders. Recent evidence suggests that miRNAs may play a crucial role in some forms of epilepsy. Work led by Prof. David Henshall at the Royal College of Surgeons in Ireland (RCSI), has identified a strong link between temporal lobe epilepsy (TLE) and increased expression of a miRNA, mir-134, known to play a crucial role in promoting dendrite outgrowth and negatively regulating spine maturation. Furthermore, they have shown that by silencing mir-134 in adult mouse models of status epilepticus using a Locked Nucleic Acid (LNA) anti miR-134 oligonucleotide, for instance antagomirs (Ant-134), they are able to powerfully suppress seizure activity and hippocampal injury caused by status epilepticus. Specifically, they demonstrated that treatment with antagomirs against mir-134 by ICV injection 24 hr prior to intra-amygdala kainic acid (KA)-induced status epilepticus, is able to significantly reduce the severity of status epilepticus recorded by EEG, as well as histological measurement of hippocampal damage (Jimenez-Mateos et al., 2012). Pretreatment of mice with ICV injection of AntimiR-134 also potently suppressed seizures induced by the chemoconvulsants pilocarpine (Jimenez-Mateos et al., 2015) and PTZ (Reschke et al., 2017). Furthermore, antagomir (ICV) treatment 1 hr. post intra-amygdala KA injection did not reduce acute status epilepticus activity, but significantly delayed the onset, and reduced total number, of spontaneous seizures monitored over 2 weeks by EEG telemetry (Jimenez-Mateos et al., 2012). Remarkably, silencing miR-134 after status epilepticus in rats resulted in 86% reduction in the subsequent occurrence of spontaneous seizures in the perforant pathway stimulation model, a toxin-free model of acquired epilepsy (Reschke et al., 2017).

The microRNA-134 related disease or disorder may be a neurological disorder, such as a neurological disorder associated with seizures, such as epilepsy or cerebral ischemic injury. Other neurological disorders which may be of interest for treatment with a microRNA-134 modulator, such as antagonist, include stroke, CNS infection-associated seizures, brain tumors, traumatic brain injury, neurodegenerative disorders, metabolic disorders causing seizures (including but not limited to hypoglycaemia, glycogen storage diseases, pyruvate dehydrogenase deficiency, acquired hypoparathyroidism, Adenylosuccinate lyase (ADSL) deficiency) and autoimmune disorders causing seizures (multiple sclerosis, diabetes melitus and systemic lupus erythematosus). The term "brain injury likely to precipitate epilepsy or seizures, or cause or have caused brain damage" should be understood to mean stroke, trauma or other types of acute neurological injuries. The microRNA-134 modulator may be used to treat or prevent seizures associated with the neurological disorder.

Contiguous Nucleotide Sequence

The term "contiguous nucleotide sequence" refers to the region of the oligonucleotide which is complementary to the target nucleic acid. The term is used interchangeably herein with the term "contiguous nucleobase sequence" and the term "oligonucleotide motif sequence".

In some embodiments all the nucleotides of the oligonucleotide constitute the contiguous nucleotide sequence. In some embodiments the oligonucleotide comprises the contiguous nucleotide sequence, and may optionally comprise further nucleotide(s), for example a nucleotide linker region which may be used to attach a functional group to the contiguous nucleotide sequence. The nucleotide linker region may or may not be complementary to the target nucleic acid. Advantageously, the contiguous nucleotide sequence is 100% complementary to the target nucleic acid (a microRNA-134 RNA, such as SEQ ID NO: 1 or 2).

Nucleotides

Nucleotides are the building blocks of oligonucleotides and polynucleotides, and for the purposes of the present invention include both naturally occurring and non-naturally occurring nucleotides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. In a preferred embodiment the modified nucleoside comprise a modified sugar moiety. The term modified nucleoside may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkages

The term "modified internucleoside linkage" is defined as generally understood by the skilled person as linkages other than phosphodiester (PO) linkages, that covalently couples two nucleosides together. The oligonucleotides of the invention may therefore comprise modified internucleoside linkages. In some embodiments, the modified internucleoside linkage increases the nuclease resistance of the oligonucleotide compared to a phosphodiester linkage. For naturally occurring oligonucleotides, the internucleoside linkage includes phosphate groups creating a phosphodiester bond between adjacent nucleosides. Modified internucleoside linkages are particularly useful in stabilizing oligonucleotides for in vivo use, and may serve to protect against nuclease cleavage at regions of DNA or RNA nucleosides in the oligonucleotide of the invention, for example within the gap region of a gapmer oligonucleotide, as well as in regions of modified nucleosides, such as region F and F'. In an embodiment, the oligonucleotide comprises one or more internucleoside linkages modified from the natural phosphodiester, such one or more modified internucleoside linkages that is for example more resistant to nuclease attack. Nuclease resistance may be determined by incubating the oligonucleotide in blood serum or by using a nuclease resistance assay (e.g. snake venom phosphodiesterase (SVPD)), both are well known in the art. Internucleoside linkages which are capable of enhancing the nuclease resistance of an oligonucleotide are referred to as nuclease resistant internucleoside linkages. In some embodiments at least 50% of the internucleoside linkages in the oligonucleotide, or contiguous nucleotide sequence thereof, are modified, such as at least 60%, such as at least 70%, such as at least 80 or such as at least 90% of the internucleoside linkages in the oligonucleotide, or contiguous nucleotide sequence thereof, are nuclease resistant internucleoside linkages. In some embodiments all of the internucleoside linkages of the oligonucleotide, or contiguous nucleotide sequence thereof, are nuclease resistant internucleoside linkages. It will be recognized that, in some embodiments the nucleosides which link the oligonucleotide of the invention to a non-nucleotide functional group, such as a conjugate, may be phosphodiester.

A preferred modified internucleoside linkage is phosphorothioate.

Phosphorothioate internucleoside linkages are particularly useful due to nuclease resistance, beneficial pharmacokinetics and ease of manufacture. In some embodiments at least 50% of the internucleoside linkages in the oligonucleotide, or contiguous nucleotide sequence thereof, are phosphorothioate, such as at least 60%, such as at least 70%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

Nucleobase

The term nucleobase includes the purine (e.g. adenine and guanine) and pyrimidine (e.g. uracil, thymine and cytosine) moiety present in nucleosides and nucleotides which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 37 1.4.1.

In a some embodiments the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA oligonucleotides, 5-methyl cytosine LNA nucleosides may be used.

Sample

The measurement of Serpine-1 biomarker may be performed in a cell extract, e.g. in an in vitro method of the invention, or may be performed in a biological extract obtained from a subject.

Biological extracts include for example a cerebrospinal fluid sample, a blood sample, or a blood plasma sample. Advantageously the sample may be a sample of cerebrospinal fluid obtained from the subject.

It will be understood that prior to the assaying the Serpine-1 biomarker the cell extract or sample may be processed, e.g. the biomarker molecule purified, for example for Serpine-1 mRNA assays, RNA may be extracted from the extract or sample.

Modified Oligonucleotide

The term modified oligonucleotide describes an oligonucleotide comprising one or more sugar-modified nucleosides and/or modified internucleoside linkages. The term chimeric" oligonucleotide is a term that has been used in the literature to describe oligonucleotides with modified nucleosides.

Complementarity

The term "complementarity" describes the capacity for Watson-Crick base-pairing of nucleosides/nucleotides. Watson-Crick base pairs are guanine (G)-cytosine (C) and adenine (A)-thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 37 1.4.1).

The term "% complementary" as used herein, refers to the number of nucleotides in percent of a contiguous nucleotide sequence in a nucleic acid molecule (e.g. oligonucleotide) which, at a given position, are complementary to (i.e. form Watson Crick base pairs with) a contiguous sequence of nucleotides, at a given position of a separate nucleic acid molecule (e.g. the target nucleic acid or target sequence). The percentage is calculated by counting the number of aligned bases that form pairs between the two sequences (when aligned with the target sequence 5'-3' and the oligonucleotide sequence from 3'-5'), dividing by the total number of nucleotides in the oligonucleotide and multiplying by 100. In such a comparison a nucleobase/nucleotide which does not align (form a base pair) is termed a mismatch.

Preferably, insertions and deletions are not allowed in the calculation of % complementarity of a contiguous nucleotide sequence.

The term "fully complementary", refers to 100% complementarity.

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned bases that are identical (a match) between two sequences (e.g. in the contiguous nucleotide sequence of the compound of the invention and in the reference sequence), dividing that number by the total number of nucleotides in the aligned region and multiplying by 100. Therefore, Percentage of Identity=(Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, *Oligonucleotides* 13:515-537). The standard state Gibbs free energy $\Delta G°$ is a more accurate representation of binding affinity and is related to the dissociation constant ($K_d$) of the reaction by $\Delta G°=-RT \ln(K_d)$, where R is the gas constant and T is the absolute temperature. Therefore, a very low $\Delta G°$ of the reaction between an oligonucleotide and the target nucleic acid reflects a strong hybridization between the oligonucleotide and target nucleic acid. $\Delta G°$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G°$ is less than zero. $\Delta G°$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for $\Delta G°$ measurements. $\Delta G°$ can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides of the present invention hybridize to a target nucleic acid with estimated $\Delta G°$ values below −10 kcal for oligonucleotides that are 10-30 nucleotides in length. In some embodiments the degree or strength of hybridization is measured by the standard state Gibbs free energy $\Delta G°$. The oligonucleotides may hybridize to a target nucleic acid with estimated $\Delta G°$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G°$ value of −10 to −60 kcal, such as −12 to −40, such as from −15 to −30 kcal or −16 to −27 kcal such as −18 to −25 kcal. Antisense oligonucleotides that target microRNA-134 are capable of hybridizing to and inhibiting (antagonizing) microRNA-134 activity.

Target Nucleic Acid

According to the present invention, the target nucleic acid is a mammalian or human microRNA-134 RNA such as SEQ ID NO: 1 or 2.

Target Sequence

The term "target sequence" as used herein refers to a sequence of nucleotides present in the target nucleic acid which comprises the nucleobase sequence which is complementary to the oligonucleotide of the invention. In some embodiments, the target sequence consists of a region on the target nucleic acid which is complementary to the contiguous nucleotide sequence of the oligonucleotide of the invention.

The oligonucleotide of the invention comprises a contiguous nucleotide sequence which is complementary to or hybridizes to the target nucleic acid, such as a sub-sequence of the target nucleic acid, such as a target sequence described herein.

The oligonucleotide comprises a contiguous nucleotide sequence which are complementary to a target sequence present in the target nucleic acid molecule. The contiguous nucleotide sequence (and therefore the target sequence) comprises of at least 7 contiguous nucleotides, such as 8, 9, 10, 11, 12, 13, 14, 15, 16, 17, 18, 19, 20, 21, 22, 23, 24, 25, 26, 27, 28, 29 or 30 contiguous nucleotides, such as from 8-22, such as from 11-18 contiguous nucleotides.

High Affinity Modified Nucleosides

A high affinity modified nucleoside is a modified nucleotide which, when incorporated into the oligonucleotide enhances the affinity of the oligonucleotide for its complementary target, for example as measured by the melting temperature ($T^m$). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclohexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'-OH group naturally found in DNA and RNA nucleosides. Substituents may, for example be introduced at the 2', 3', 4' or 5' positions.

2' Sugar Modified Nucleosides.

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' substituted nucleosides, and numerous 2' substituted nucleosides have been found to have beneficial properties when incorporated into oligonucleotides. For example, the 2' modified sugar may provide enhanced binding affinity and/ or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

Locked Nucleic Acids (LNA)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667.

Further non limiting, exemplary LNA nucleosides are disclosed in Scheme 1.

Scheme 1:

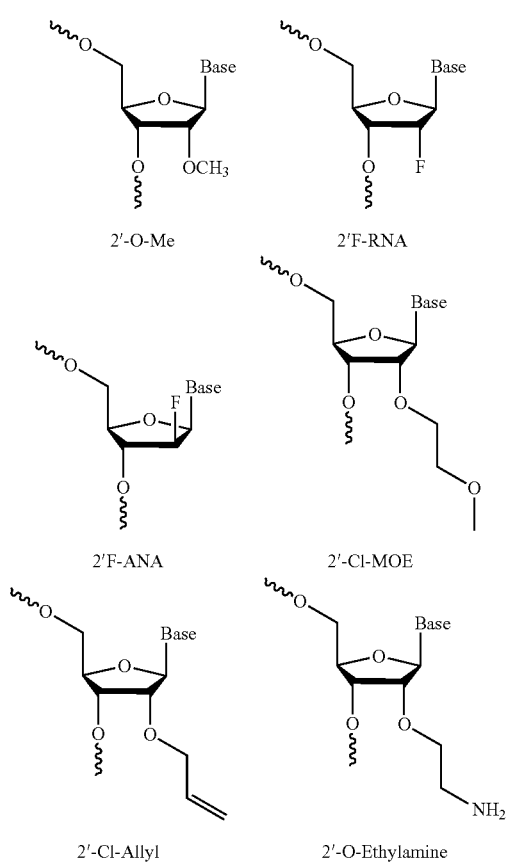

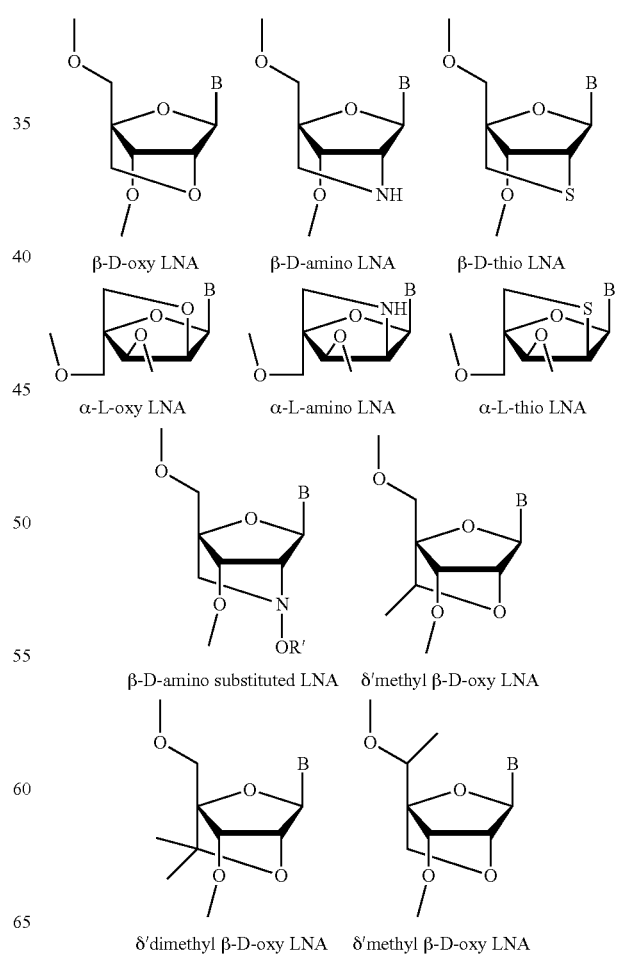

In relation to the present invention 2' substituted does not include 2' bridged molecules like LNA.

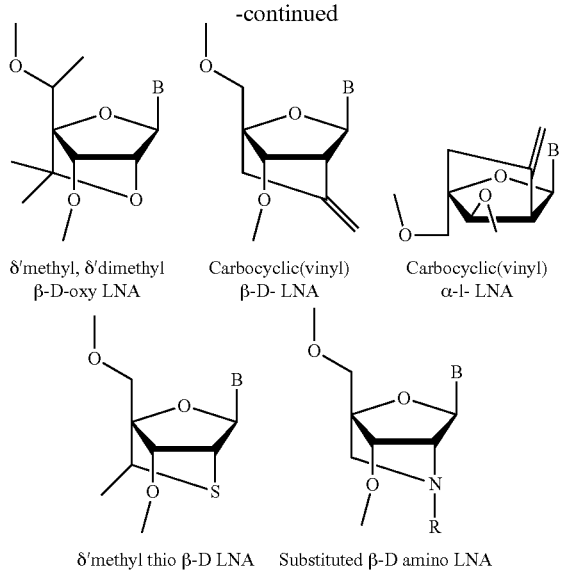

δ'methyl, δ'dimethyl β-D-oxy LNA    Carbocyclic(vinyl) β-D- LNA    Carbocyclic(vinyl) α-l- LNA δ'methyl thio β-D LNA    Substituted β-D amino LNA Particular LNA nucleosides are beta-D-oxy-LNA, 6'-methyl-beta-D-oxy LNA such as (S)-6'-methyl-beta-D-oxy-LNA (ScET) and ENA.

A particularly advantageous LNA is beta-D-oxy-LNA.

Non RNase H Recruiting Antisense Oligonucleotides

WO2005/013901 disclosed RNaseH recruiting 2'-O-MOE gapmers, and fully 2-O-MOE modified oligonucleotides for the inhibition of microRNAs. In general RNAseH recruiting gapmer oligonucleotides are considered to be inferior to non RNaseH recruiting steric block antisense oligonucleotides for inhibition of microRNAs (see Davis et al. 2006 Nucleic Acids Res 34-2294-304). Krützfelt et al. 2005 Nature 438 685-9 discloses fully 2'O-methyl modified antisense oligonucleotide cholesterol conjugates, which are incapable of recruiting RNaseH which were effective at inhibiting microRNA-122 in vivo.

As disclosed in WO2007/112754 for inhibition of microRNAs it is advantageous to use non RNaseH recruiting high affinity antisense oligoucleoitdes, such as LNA antimiRs.

EP 1 222 309 provides in vitro methods for determining RNaseH activity, which may be used to determine the ability to recruit RNaseH. A oligomer is deemed capable of recruiting RNase H if, when provided with the complementary RNA target, it has an initial rate, as measured in pmol/l/min, of at least 1%, such as at least 5%, such as at least 10% or less than 20% of the equivalent DNA only oligonucleotide, with no 2' substitutions, with phosphorothioate linkage groups between all nucleotides in the oligonucleotide, using the methodology provided by Example 91-95 of EP 1 222 309.

In one embodiment In some embodiments, an oligomer is deemed essentially incapable of recruiting RNaseH if, when provided with the complementary RNA target, and RNaseH, the RNaseH initial rate, as measured in pmol/1/min, is less than 1%, such as less than 5%, such as less than 10% or less than 20% of the initial rate determined using the equivalent DNA only oligonucleotide, with no 2' substitutions, with phosphorothioate linkage groups between all nucleotides in the oligonucleotide, using the methodology provided by Example 91-95 of EP 1 222 309.

Totalmers

In some embodiments, the oligomer or contiguous nucleotide sequence thereof consists of a contiguous sequence of nucleoside analogues, such as affinity enhancing nucleoside analogues—referred to herein is as a 'totalmer'.

A totalmer is a single stranded oligomer, or contiguous nucleotide sequence thereof, which does not comprise DNA or RNA nucleosides, and as such only comprises nucleoside analogue nucleosides. The oligomer, or contiguous nucleotide sequence thereof, maybe a totalmer—indeed various totalmer designs are highly effective as therapeutic oligomers, particularly when targeting microRNA (antimiRs) or as splice switching oligomers (SSOs).

In some embodiments, the totalmer comprises or consists of at least one XYX or YXY sequence motif, such as a repeated sequence XYX or YXY, wherein X is LNA and Y is an alternative (i.e. non LNA) nucleotide analogue, such as a 2'-OMe RNA unit and 2'-fluoro DNA unit. The above sequence motif may, in some embodiments, be XXY, XYX, YXY or YYX for example.

In some embodiments, the totalmer may comprise or consist of a contiguous nucleotide sequence of between 8 and 16 nucleotides, such as 9, 10, 11, 12, 13, 14, or 15 nucleotides, such as between 8 and 12 nucleotides.

In some embodiments, the contiguous nucleotide sequence of the totalmer comprises of at least 30%, such as at least 40%, such as at least 50%, such as at least 60%, such as at least 70%, such as at least 80%, such as at least 90%, such as 95%, such as 100% LNA units. The remaining units may be selected from the non-LNA nucleotide analogues referred to herein in, such as those selected from the group consisting of 2'-O_alkyl-RNA unit, 2'-OMe-RNA unit, 2'-amino-DNA unit, 2'-fluoro-DNA unit, LNA unit, PNA unit, HNA unit, INA unit, and a 2'MOE RNA unit, or the group of 2'-OMe RNA unit and 2'-fluoro DNA unit.

In some embodiments the totalmer consist or comprises of a contiguous nucleotide sequence which consists only of LNA units.

In some embodiments, the totalmer may be targeted against a microRNA (i.e. be antimiRs)—as referred to in U.S. provisional applications 60/979,217 and 61/028,062, and PCT/DK2008/000344, all of which are hereby incorporated by reference.

Mixmers

The term 'mixmer' refers to oligomers, or contiguous nucleotide sequences thereof, which comprise DNA nucleosides and nucleoside analogue nucleosides, where, as opposed to gapmers, tailmers, headmers and blockmers, there is no contiguous sequence of more 4 or more than 5 naturally occurring DNA nucleosides (i.e. a region od DNAs which is sufficient to enable RNaseH recruitment activity).

The oligomer, or contiguous nucleotide sequence thereof, may be mixmers—indeed various mixmer designs are highly effective as therapeutic oligomers, particularly when targeting microRNA (antimiRs), microRNA binding sites on mRNAs (Blockmirs) or as splice switching oligomers (SSOs).

The oligomer may, or contiguous nucleotide sequence thereof, in some embodiments, also be a mixmer and indeed, due to the ability of mixmers to effectively and specifically bind to their target, the use of mixmers as therapeutic oligomers are considered to be particularly effective in decreasing the target RNA.

In some embodiments, the mixmer comprises or consists of a contiguous nucleotide sequence of repeating pattern of nucleotide analogue and naturally occurring nucleotides, or one type of nucleotide analogue and a second type of nucleotide analogues. The repeating pattern, may, for instance be every second or every third nucleotide is a nucleotide analogue, such as LNA, and the remaining nucleotides are naturally occurring nucleotides, such as DNA, or are a 2'substituted nucleotide analogue such as 2'MOE of 2'fluoro analogues as referred to herein, or, in some embodiments selected form the groups of nucleotide analogues referred to herein. It is recognised that the repeating pattern of nucleotide analogues, such as LNA units, may be combined with nucleotide analogues at fixed positions— e.g. at the 5' or 3' termini.

In some embodiments the first nucleotide of the oligomer or mixmer, counting from the 3' end, is a nucleotide analogue, such as an LNA nucleotide.

In some embodiments, which maybe the same or different, the second nucleotide of the oligomer or mixmer, counting from the 3' end, is a nucleotide analogue, such as an LNA nucleotide.

In some embodiments, which maybe the same or different, the seventh and/or eighth nucleotide of the oligomer or mixmer, counting from the 3' end, are nucleotide analogues, such as LNA nucleotides.

In some embodiments, which maybe the same or different, the ninth and/or the tenth nucleotides of the oligomer or mixmer, counting from the 3' end, are nucleotide analogues, such as LNA nucleotides.

In some embodiments, which maybe the same or different, the 5' terminal of the oligomer or mixmer is a nucleotide analogue, such as an LNA nucleotide.

The above design features may, in some embodiments be incorporated into the mixmer design, such as antimiR mixmers.

In some embodiments, the mixmer does not comprise a region of more than 4 consecutive DNA nucleotide units or 3 consecutive DNA nucleotide units. In some embodiments, the mixmer does not comprise a region of more than 2 consecutive DNA nucleotide units.

In some embodiments, the mixmer comprises at least a region consisting of at least two consecutive nucleotide analogue units, such as at least two consecutive LNA units.

In some embodiments, the mixmer comprises at least a region consisting of at least three consecutive nucleotide analogue units, such as at least three consecutive LNA units.

In some embodiments, the mixmer of the invention does not comprise a region of more than 7 consecutive nucleotide analogue units, such as LNA units. In some embodiments, the mixmer of the invention does not comprise a region of more than 6 consecutive nucleotide analogue units, such as LNA units. In some embodiments, the mixmer of the invention does not comprise a region of more than 5 consecutive nucleotide analogue units, such as LNA units. In some embodiments, the mixmer of the invention does not comprise a region of more than 4 consecutive nucleotide analogue units, such as LNA units. In some embodiments, the mixmer of the invention does not comprise a region of more than 3 consecutive nucleotide analogue units, such as LNA units. In some embodiments, the mixmer of the invention does not comprise a region of more than 2 consecutive nucleotide analogue units, such as LNA units.

In the mixmer embodiments, which refer to the modification of nucleotides in positions 3 to 8, counting from the 3' end, the LNA units may be replaced with other nucleotide analogues, such as those referred to herein. "X" may, therefore be selected from the group consisting of 2'-O-alkyl-RNA unit, 2'-OMe-RNA unit, 2'-amino-DNA unit, 2'-fluoro-DNA unit, 2'-MOE-RNA unit, LNA unit, PNA unit, HNA unit, INA unit. "x" is preferably DNA or RNA, most preferably DNA.

In some embodiments, the mixmer, such as an antimiR mixmer, is modified in positions 3 to 8—i.e. comprises at least one nucleotide analogue in positions 3 to 8, counting from the 3' end. The design of this sequence may be defined by the number of non-LNA units present or by the number of LNA units present. In some embodiments of the former, at least one, such as one, of the nucleotides in positions three to eight, counting from the 3' end, is a non-LNA unit. In some embodiments, at least two, such as two, of the nucleotides in positions three to eight, counting from the 3' end, are non-LNA units. In some embodiments, at least three, such as three, of the nucleotides in positions three to eight, counting from the 3' end, are non-LNA units. In some embodiments, at least four, such as four, of the nucleotides in positions three to eight, counting from the 3' end, are non-LNA units. In some embodiments, at least five, such as five, of the nucleotides in positions three to eight, counting from the 3' end, are non-LNA units. In some embodiments, all six nucleotides in positions three to eight, counting from the 3' end, are non-LNA units.

Alternatively defined, in some embodiments, the mixmer, such as an antimiR mixmer, according to the invention comprises at least one LNA unit in positions three to eight, counting from the 3' end. some embodiments, the mixmer, such as an antimiR mixmer, comprises one LNA unit in positions three to eight, counting from the 3' end. The substitution pattern for the nucleotides in positions three to eight, counting from the 3' end, may be selected from the group consisting of Xxxxxx, xXxxxx, xxXxxx, xxxXxx, xxxxXx and xxxxxX, wherein "X" denotes an LNA unit and "x" denotes a non-LNA unit.

In some embodiments, the mixmer, such as an antimiR mixmer, comprises at least two LNA units in positions three to eight, counting from the 3' end. In some embodiments thereof, the mixmer comprises two LNA units in positions three to eight, counting from the 3' end. The substitution pattern for the nucleotides in positions three to eight, counting from the 3' end, may be selected from the group consisting of XXxxxx, XxXxxx, XxxXxx, XxxxXx, XxxxxX, xXXxxx, xXxXxx, xXxxXx, xXxxxX, xxXXxx, xxXxXx, xxXxxX, xxxXXx, xxxXxX and xxxxXX, wherein "X" denotes an LNA unit and "x" denotes a non-LNA unit. In an embodiment, the substitution pattern for the nucleotides in positions three to eight, counting from the 3' end, is selected from the group consisting of XxXxxx, XxxXxx, XxxxXx, XxxxxX, xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx, xXxxxX, xxXxXx, xxXxxX and xxxXxX, wherein "X" denotes an LNA unit and "x" denotes a non-LNA unit. In some embodiments, the substitution pattern for the nucleotides in positions three to eight, counting from the 3' end, is selected from the group consisting of xXxXxx, xXxxXx and xxXxXx, wherein "X" denotes an LNA unit and "x" denotes a non-LNA unit. In some embodiments, the substitution pattern for the nucleotides in positions three to eight, counting from the 3' end, is xXxXxx, wherein "X" denotes an LNA unit and "x" denotes a non-LNA unit.

In some embodiments, the mixmer, such as an antimiR mixmer, comprises at least three LNA units in positions three to eight, counting from the 3' end. In an embodiment thereof, the mixmer comprises three LNA units in positions three to eight, counting from the 3' end. The substitution pattern for the nucleotides in positions three to eight, counting from the 3' end, may be selected from the group consisting of XXXxxx, xXXXxx, xxXXXx, xxxXXX, XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In some embodiments, the substitution pattern for the nucleotides in positions three to eight, counting from the 3' end, is selected from the group consisting of XXxXxx, XXxxXx, XXxxxX, xXXxXx, xXXxxX, xxXXxX, XxXXxx, XxxXXx, XxxxXX, xXxXXx, xXxxXX, xxXxXX, xXxXxX and XxXxXx, wherein "X" denotes an LNA unit and "x" denotes a non-LNA unit. In some embodiments, the substitution pattern for the nucleotides in positions three to eight, counting from the 3' end, is selected from the group consisting of xXXxXx, xXXxxX, xxXXxX, xXxXXx, xXxxXX, xxXxXX and xXxXxX, wherein "X" denotes an LNA unit and "x" denotes a non-LNA unit. In some embodiments, the substitution pattern for the nucleotides in positions three to eight, counting from the 3' end, is xXxXxX or XxXxXx, wherein "X" denotes an LNA unit and "x" denotes a non-LNA unit. In some embodiments, the substitution pattern for the nucleotides in positions three to eight, counting from the 3' end, is xXxXxX, wherein "X" denotes an LNA unit and "x" denotes a non-LNA unit.

In some embodiments, the mixmer comprises at least four LNA units in positions three to eight, counting from the 3' end. In some embodiments thereof, the mixmer comprises four LNA units in positions three to eight, counting from the 3' end. The substitution pattern for the nucleotides in positions three to eight, counting from the 3' end, may be selected from the group consisting of xxXXXX, xXxXXX, xXXxXX, xXXXxX, xXXXXx, XxxXXX, XxXxXX, XxXXxX, XxXXXx, XXxxXX, XXxXxX, XXxXXx, XXXxxX, XXXxXx and XXXXxx, wherein "X" denotes an LNA unit and "x" denotes a non-LNA unit.

In some embodiments, the mixmer according to the present invention comprises at least five LNA units in positions three to eight, counting from the 3' end. In some embodiments thereof, the mixmercomprises five LNA units in positions three to eight, counting from the 3' end. The substitution pattern for the nucleotides in positions three to eight, counting from the 3' end, may be selected from the group consisting of xXXXXX, XxXXXX, XXxXXX, XXXxXX, XXXXxX and XXXXXx, wherein "X" denotes an LNA unit and "x" denotes a non-LNA unit.

In some embodiments, said non-LNA unit is another nucleotide analogue unit.

In some mixmer embodiments the substitution pattern for the nucleotides from position 11, counting from the 3' end, to the 5' end may include nucleotide analogue units (such as LNA) or it may not. In some embodiments, the mixmer comprises at least one nucleotide analogue unit (such as LNA), such as one nucleotide analogue unit, from position 11, counting from the 3' end, to the 5' end. In some embodiments, the mixmer comprises at least two nucleotide analogue units, such as LNA units, such as two nucleotide analogue units, from position 11, counting from the 3' end, to the 5' end.

In some embodiments which refer to the modification of nucleotides in the nucleotides from position 11 to the 5' end of the oligomer, the LNA units may be replaced with other nucleotide anlogues, such as those referred to herein. "X" may, therefore be selected from the group consisting of 2'-O-alkyl-RNA unit, 2'-OMe-RNA unit, 2'-amino-DNA unit, 2'-fluoro-DNA unit, LNA unit, PNA unit, HNA unit, INA unit. "x" is preferably DNA or RNA, most preferably DNA.

In some embodiments, the mixmer has the following substitution pattern, which is repeated from nucleotide eleven, counting from the 3' end, to the 5' end: xXxX or XxXx, wherein "X" denotes an LNA unit and "x" denotes a non-LNA unit. In another embodiment, the mixmer has the following substitution pattern, which is repeated from nucleotide eleven, counting from the 3' end, to the 5' end: XXxXxx, XXxxXx or XxXxxX, wherein "X" denotes an LNA unit and "x" denotes a non-LNA unit. In yet another embodiment, the mixmer has the following substitution pattern, which is repeated from nucleotide eleven, counting from the 3' end, to the 5' end: XXXxXXXx, XXxXxXxX, XXXxxxXX or XXxXxxXX, wherein "X" denotes an LNA unit and "x" denotes a non-LNA unit.

The specific substitution pattern for the nucleotides from position 11, counting from the 3' end, to the 5' end depends on the number of nucleotides in the mixmer. In a preferred embodiment, the mixmer contains 12 nucleotides and the substitution pattern for positions 11 to 12, counting from the 3' end, is selected from the group consisting of xX and Xx, wherein "X" denotes an LNA unit and "x" denotes a non-LNA unit. In some embodiments, the substitution pattern for positions 11 to 12, counting from the 3' end, is xX, wherein "X" denotes an LNA unit and "x" denotes a non-LNA unit. Alternatively, no LNA units are present in positions 11 to 12, counting from the 3' end, i.e. the substitution pattern is xx.

In some embodiments, the mixmer contains 12 nucleotides and the substitution pattern for positions 10 to 12, counting from the 3' end, is selected from the group consisting of Xxx, xXx, xxX, XXx, XxX, xXX and XXX, wherein "X" denotes an LNA unit and "x" denotes a non-LNA unit. In some embodiments thereof, the substitution pattern for positions 10 to 12, counting from the 3' end, is selected from the group consisting of xXx, xxX and xXX, wherein "X" denotes an LNA unit and "x" denotes a non-LNA unit. In some embodiments, the substitution pattern for positions 10 to 12, counting from the 3' end, is xxX, wherein "X" denotes an LNA unit and "x" denotes a non-LNA unit. Alternatively, no LNA units are present in positions 10 to 12, counting from the 3' end, i.e. the substitution pattern is xxx.

In some embodiments, the mixmer contains an LNA unit at the 5' end. In some embodiments, the mixmer contains an LNA unit at the first two positions, counting from the 5' end. The mixmer may also contain one or more of the structural features which are specified in the context of the antimiR herein—either the context that the mixmer contains a similar pattern and number of nucleotides/nucleotide analogues (e.g. X and x or X and Y).

Conjugate

The term conjugate as used herein refers to an oligonucleotide which is covalently linked to a non-nucleotide moiety (conjugate moiety or region C or third region).

Conjugation of the oligonucleotide of the invention to one or more non-nucleotide moieties may improve the pharmacology of the oligonucleotide, e.g. by affecting the activity, cellular distribution, cellular uptake or stability of the oligonucleotide. In some embodiments the conjugate moiety modify or enhance the pharmacokinetic properties of the oligonucleotide by improving cellular distribution, bioavailability, metabolism, excretion, permeability, and/or cellular uptake of the oligonucleotide. In particular the conjugate may target the oligonucleotide to a specific organ, tissue or cell type and thereby enhance the effectiveness of the oligonucleotide in that organ, tissue or cell type. A the same time the conjugate may serve to reduce activity of the oligonucleotide in non-target cell types, tissues or organs, e.g. off target activity or activity in non-target cell types, tissues or organs.

In an embodiment, the non-nucleotide moiety (conjugate moiety) is selected from the group consisting of carbohydrates, cell surface receptor ligands, drug substances, hormones, lipophilic substances, polymers, proteins, peptides, toxins (e.g. bacterial toxins), vitamins, viral proteins (e.g. capsids) or combinations thereof.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence or gapmer region F-G-F' (region A).

In some embodiments of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Region B refers to biocleavable linkers comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from proteolytic enzymes or hydrolytic enzymes or nucleases. In one embodiment the biocleavable linker is susceptible to S1 nuclease cleavage. DNA phosphodiester containing biocleavable linkers are described in more detail in WO 2014/076195 (hereby incorporated by reference)—see also region D' or D" herein.

Region Y refers to linkers that are not necessarily biocleavable but primarily serve to covalently connect a conjugate moiety (region C or third region), to an oligonucleotide (region A or first region). The region Y linkers may comprise a chain structure or an oligomer of repeating units such as ethylene glycol, amino acid units or amino alkyl groups. The oligonucleotide conjugates of the present invention can be constructed of the following regional elements A-C, A-B-C, A-B-Y-C, A-Y-B-C or A-Y-C. In some embodiments the linker (region Y) is an amino alkyl, such as a C2-C36 amino alkyl group, including, for example C6 to C12 amino alkyl groups. In a preferred embodiment the linker (region Y) is a C6 amino alkyl group.

Treatment

The term 'treatment' as used herein refers to both treatment of an existing disease (e.g. a disease or disorder as herein referred to), or prevention of a disease, i.e. prophylaxis. It will therefore be recognized that treatment as referred to herein may, in some embodiments, be prophylactic.

EXAMPLES

Summary miR-134 has an important regulatory role in epilepsy (Jimenez-Mateos et al. 2012), however the mechanism of action of miR-134 in epilepsy is still unclear. To identify potential targets for miR-134, primary cortical neurons were treated with an LNA-antimiR inhibitor of miR-134 and incubated for 6 days. After the incubation period, RNA from the cells was isolated and global RNA sequencing analysis was performed to identify mRNAs whose expression was modulated by the inhibition of microRNA-134. From the de-repressed mRNAs identified, we identified genes which were significantly de-repressed and also harboured putative microRNA-134 binding sites, based upon the presence of a potential microRNA-134 seed sequence within their 3'UTR. These candidate biomarker transcripts were experimentally validated in an additional experiment using primary cortical neurons treated with a range of concentrations of LNA-antimiR-134. Of the candidate transcripts tested, one Serpine1, was validated and was both de-repressed and regulated in a dose-dependent manner. Serpine1 encodes the protein Plasminogen activator inhibitor-1 (PAI-1) that binds and inhibits tissue plasminogen activator (tPA). A causal role of tPA in epilepsy has been shown as tPA knockout mice are protected against chemical induced epilepsy (Tsirka et al., 1995). This presents a potential mechanism by which microRNA-134 may modulate epilepsy, were inhibition of miR-134 de-represses Serpine1/PAI-1 leading to inhibition of tPA. Serpine1/PAI-1 or active tPA are biomarkers for the inhibition of miR-134, not just at mRNA levels but also at protein levels and activity levels in biological fluids like cerebrospinal fluid.

Jimenez-Mateos et al., Silencing microRNA-134 produces neuroprotective and prolonged seizure-suppressive effects. Nat Med. 2012 July; 18(7):1087-94.

Tsirka S E, et al., showed that excitotoxin-induced neuronal degeneration and seizure are mediated by tissue plasminogen activator. Nature. 1995 Sep. 28; 377(6547):340-4.

Example 1: RNA Sequencing Analysis of RNA Isolated from Mouse Primary Cortical Neurons after Treatment with Inhibitor of miR-134, AntimiR, for 6 Days Identifies Potential miR-134 Targets A cholesterol conjugated LNA antimiR supplied by Exiqon was used in this example.

Primary cultures of mouse neuronal cultures were prepared from P1 pups and plated in 6 multi-well plates as described (Chen et al., 2007). After 6 days in vitro (DIV) mouse primary neuronal cultures were further treated for 6 days with either Mock (n=6) or 0.1 µM (n=3) miR-134 inhibitor AntimiR (Exiqon, LNA-modified and 3' cholesterol-modified oligonucleotides). The neuronal cells were cultured in basal growth Medium with the oligonucleotides added in PBS. RNA from the 6 well setup were purified by MagNA Pure 96, Cellular RNA Large Volume Kit (Roche, ID:05469535001), according to the manufacturer's instructions with 50 µL elution volume. RNA sequencing (100 million paired end reads) after ribosomal depletion was performed by Eurofins Genomics.

Paired-end Fastq files obtained from the illumina sequencing experiment were aligned to the mouse genomic sequence (UCSC Genome Browser assembly ID: mm10) using hisat2 version 2.1.0 (Kim, Langmead, and Salzberg 2015) with default settings except "-rna-strandness RF". Mapped reads were filtered based on mapping quality (column 5 of the SAM file), which was required to be at least 10, and a SAM flag (column 2 of the SAM file), in which the attribute "read mapped in a proper pair" must be true. Mapped reads were summarized using function featureCounts from Rsubread R package version 1.28.1 (Liao, Smyth, and Shi 2013) using mouse ENSEMBL gene annotation version 92 (using "havana" and "ensemble or havana" genes only; ensembl.org), with settings "isPairedEnd=TRUE, requireBothEndsMapped=TRUE, strandSpecific=2, juncCounts=TRUE, allowMultiOverlap=FALSE". Differential gene expression was performed using voom method of limma R package, version 3.34.9 (Law et al. 2014) as described in a limma R package user guide (bioconductor.org First edition: 2 Dec. 2002, Last revised: 15 Apr. 2018).

MicroRNA seed sequence is a 6-8 nucleotide long region of a microRNA, which needs to perfectly hybridize with the target sequence in a 3' untranslated region (3' UTR) of the mRNA (Ellwanger et al. 2011). To identify if a given gene harbors miR-134 seed sequence matches, we counted the number of occurrences of a 7-mer sequence "CAGTCAC", which perfectly matches miR-134 seed sequence defined as a 7-mer starting at position 2 of the miRNA-134, in a 3' UTR for a given gene (for genes with multiple annotated 3' UTRs, the maximum count is presented).

Results: RNA sequencing analysis identifies significantly regulated genes after 6 days treatment of primary mouse cortical neurons with 0.1 µM miR-134 AntimiR. Volcano plot (FIG. 1) showing differences in gene expression between control Mock treated primary cortical neurons and primary cortical neurons treated with 0.1 µM miR-134 AntimiR (top panel, upregulated genes to the right and downregulated genes to the left). Each point corresponds to a gene. Genes, whose expression level differs between those two conditions with multiple testing adjusted P-value <0.05 are labeled with gene names Significantly upregulated genes with a 7-oligonucleotide miR-134 seed sequence encompass Serpine1, Gpr35, Syt6, Peg10, Olfr460—See Table 1:

cytosines are 5-methyl cytosine, and all internucleoside linkages are phosphorothioate internucleoside linkages Treatment of primary mouse cortical neurons with the miR-134 LNA inhibitor, AntimiR, induces expression of Serpine1 mRNA and not of Syt6, Gpr35 or Peg10 mRNA. Primary cultures of mouse neuronal cultures were prepared from P1 pups and plated in 24 multi-well plates as described (Chen et al., 2007). After 6 days in vitro (DIV) Mouse neuronal cultures were further treated for 5 days with mock (n=4) or 0.04 µM, 0.11 µM, 0.33 µM, 1 µM, or 3 µM (n=4) miR-134 inhibitor LNA-AntimiR. RNA was purified by MagNA Pure 96, Cellular RNA Large Volume Kit (Roche, ID:05469535001), according to the manufacturer's instructions with 50 µL elution volume. cDNA was synthesized using iScript Advanced cDNA Synthesis Kit for qPCR (BIO-RAD, ID:1725038), according to the manufacturer's instructions. To prevent inhibition of the cDNA synthesis, RNA was denatured for one minute at 90° C. before cDNA synthesis. ddPCR was performed using ddPCR™ Supermix for Probes (No dUTP) (BIORAD, ID:186-3024). FAM labeled Probe and primers were from IDT (Serpine1 Mm.PT.58.6413525; Syt6 Mm.PT.58.5412202, Peg10 Mm.PT.58.12887449, Gpr25 Mm.PT.58.6713348), whereas HEX-labeled Tbp Probe and primers were from BIO-RAD (Cat #10031256). The cycling conditions were: 95° C. for 10 minutes, denaturation at 94° C. for 30 seconds, annealing temperature depending on the assay for 1 minute, repeating the denaturing and annealing step 42 times. After 42 cycles, enzyme was deactivated at 98° C. for 10 minutes. If the samples were not used directly they were stored at 4° C. The droplets were streamed through the droplet reader QX200™ (BIO-RAD) for flourescence analysis and the number of FAM-coloured Serpine1 droplets and HEX-coloured Tbp droplets were counted.

Example 3

Potential miR-134 target site in Serpine1 was identified using TargetScanHuman 7.1 and a potential hybridization of miR-134 seed sequence with 3' UTR Serpine1 mRNA was identified at position 345-352 in mouse transcript and at

TABLE 1

| Ensembl ID | Gene name | logFC | AveExpr | P. Value | adj. P. Val | Seed matches |
|---|---|---|---|---|---|---|
| ENSMUSG00000037411 | Serpine1 | 0.96 | 4.89 | 5.03E−07 | 0.00264181 | 1 |
| ENSMUSG00000020447 | Npc1l1 | 1.70 | 2.26 | 5.27E−07 | 0.00264181 | 0 |
| ENSMUSG00000026271 | Gpr35 | 1.19 | 3.46 | 1.42E−06 | 0.00465327 | 1 |
| ENSMUSG00000027792 | Bche | 0.90 | 3.57 | 1.72E−06 | 0.00465327 | 0 |
| ENSMUSG00000040152 | Thbs1 | 0.67 | 6.26 | 1.86E−06 | 0.00465327 | 0 |
| ENSMUSG00000026579 | F5 | 0.77 | 3.28 | 6.60E−06 | 0.01102312 | 0 |
| ENSMUSG00000027849 | Syt6 | 0.38 | 5.70 | 1.01E−05 | 0.01383517 | 1 |
| ENSMUSG00000031762 | Mt2 | 0.71 | 4.24 | 2.35E−05 | 0.0252597 | 0 |
| ENSMUSG00000049723 | Mmp12 | 1.17 | 3.10 | 2.73E−05 | 0.02734967 | 0 |
| ENSMUSG00000068587 | Mgam | 1.74 | 0.96 | 1.17E−05 | 0.01441299 | 0 |
| ENSMUSG00000016356 | Col20a1 | 0.62 | 4.81 | 3.47E−05 | 0.03068922 | 0 |
| ENSMUSG00000067206 | Lrrc66 | 1.84 | 0.61 | 1.25E−05 | 0.01441299 | 0 |
| ENSMUSG00000092035 | Peg10 | 0.55 | 6.87 | 5.30E−05 | 0.04167564 | 1 |
| ENSMUSG00000036292 | Gramd1c | 1.00 | 2.47 | 7.58E−05 | 0.04559284 | 0 |
| ENSMUSG00000045514 | Olfr460 | 1.76 | 0.26 | 8.07E−05 | 0.04605006 | 1 |
| ENSMUSG00000037577 | Ephx3 | 2.49 | −0.96 | 8.27E−05 | 0.04605006 | 0 |

Example 2

The compound used in this example was a non conjugated LNA antimiR of sequence: 5' TgGtcAAccAgTcAC 3' (SEQ ID NO: 8), wherein capital letters are beta-D-oxy-LNA nucleosides, lower case letters are DNA nucleosides, LNA position 417-424 Serpine 3' UTR in the human transcript (See FIG. 3). Interaction between microRNA-134 and 3'UTR fragment was predicted using RNAStructure "Predict a Bimolecular Secondary Structure Web Server" version 6.0.1 (/rna.urmc.rochester.edu) (Reuter and Mathews 2010).

Example 4

Expression analysis of Serpine1 mRNA in human breast cancer MDA-MB-231 cells after treatment with premiR-134 and LNA antimiR or LNA control. MDA-MB-231 were seeded in 24-well plates and the day after transfected with 40 nM premiR-134 (Ambion Pre-miR miRNA Precursors hsa-mir-134-5p, AM17100) or/and 100 nM LNA antimiR or 100 nM Control LNA using lipofectamine 2000 (Invitrogen) according to manufacturer's instruction. Two days after transfection, RNA from the 24 well setup were purified by MagNA Pure 96, Cellular RNA Large Volume Kit (Roche, ID:05469535001), according to the manufacturer's instructions with 50 µL elution volume. One step ddPCR was performed using One-Step RT-ddPCR Advanced Kit for Probes (BIORAD, ID:1864021). FAM labeled Probe and primers were from IDT (Serpine1 Hs.PT.58.3938488.g), whereas HEX-labeled HPRT1 probe and primers were from IDT (Hs.PT.58v.45621572). The cycling conditions were: 95° C. for 10 minutes, denaturation at 94° C. for 30 seconds, annealing temperature depending on the assay for 1 minute, repeating the denaturing and annealing step 42 times. After 42 cycles, enzyme was deactivated at 98° C. for 10 minutes. If the samples were not used directly they were stored at 4° C. The droplets were streamed through the droplet reader QX200™ (BIO-RAD) for flourescence analysis and the number of FAM-coloured Serpine1 droplets and HEX-coloured HPRT1 droplets were counted. Results shown in FIG. 4.

FURTHER REFERENCES

Chen Y. et al., Nat Protoc. 2007; 2(5):1044-51.
Ellwanger et al., 2011. "The Sufficient Minimal Set of MiRNA Seed Types." *Bioinformatics* (Oxford, England) 27 (10): 1346-50.
Kim, et al., 2015. "HISAT: A Fast Spliced Aligner with Low Memory Requirements." *Nature Methods* 12 (4): 357-60.
Law, et al., 2014. "Voom: Precision Weights Unlock Linear Model Analysis Tools for RNA-Seq Read Counts." *Genome Biology* 15 (2): R29.
Liao, et al., 2013. "The Subread Aligner: Fast, Accurate and Scalable Read Mapping by Seed-and-Vote." *Nucleic Acids Research* 41 (10): e108.
Reuter, Jessica S., and David H. Mathews. 2010. "RNA-structure: Software for RNA Secondary Structure Prediction and Analysis." BMC Bioinformatics 11 (March): 129.

---

The invention claimed is:

1. An in vitro method for determining the activity of a microRNA-134 modulator in a cell, which is a neuronal cell or breast cancer cell, said method comprising a) a step of determining the level of a Serpine 1 biomarker in the cell, to which a microRNA-134 modulator has been added, b) comparing the level of the Serpine 1 biomarker determined step a) with at least one reference level of the Serpine 1 biomarker;

wherein an elevation in Serpine 1 biomarker as compared to the reference level is indicative of a reduced level of microRNA-134, and a decrease in Serpine 1 biomarker as compared to the reference level is indicative of an increased level of microRNA-134, and wherein the microRNA-134 modulator is an antisense oligonucleotide inhibitor of microRNA-134, and wherein the step of determining the level of a Serpine 1 biomarker in the cell is by measuring Serpine 1 mRNA.

2. The method according to claim 1, wherein the cell is from a subject who is suffering from a disease or disorder associated with microRNA-134, or is likely to develop said disease or disorder associated with microRNA-134.

3. The method according to claim 1, wherein the cell is from a subject has previously undergone tPA (tissue plasminogen activator) treatment.

4. The method according to claim 1, wherein the Serpine 1 biomarker is assayed from cells found in a sample obtained from a subject, and wherein the sample is selected from the group consisting of a cerebrospinal fluid sample and a blood sample.

5. The method according to claim 4, wherein the sample is a cerebrospinal fluid sample.

6. The method according to claim 1, wherein the microRNA-134 modulator is an antisense oligonucleotide inhibitor of microRNA-134 which comprises at least 7 contiguous nucleotides which are complementary to microRNA-134.

7. The method according to claim 1, wherein the microRNA-134 modulator is an LNA antisense oligonucleotide.

8. The method according to claim 2, wherein the disease or disorder associated with microRNA-134 is a neurological disorder, a disorder associated with seizures, epilepsy, epileptic encephalopathies, or cerebral ischemic injury.

9. The method according to claim 6, wherein the microRNA-134 modulator is an antisense oligonucleotide inhibitor of microRNA-134 which comprises at least 7 contiguous nucleotides which are fully complementary to microRNA-134.

10. The method according to claim 6, wherein the microRNA-134 modulator is an antisense oligonucleotide inhibitor of microRNA-134 which comprises at least 7 contiguous nucleotides which are complementary to hsa-miR-134 or SEQ ID NO: 1.

* * * * *

SEQUENCE LISTING

```
<160> NUMBER OF SEQ ID NOS: 10

<210> SEQ ID NO 1
<211> LENGTH: 22
<212> TYPE: RNA
<213> ORGANISM: homo sapiens

<400> SEQUENCE: 1
ugugacuggu ugaccagagg gg                                             22

<210> SEQ ID NO 2
<211> LENGTH: 73
<212> TYPE: RNA
<213> ORGANISM: Homo sapiens

<400> SEQUENCE: 2
cagggugugu gacugguuga ccagaggggc augcacugug uucacccugu gggccaccua    60
gucaccaacc cuc                                                       73

<210> SEQ ID NO 3
<211> LENGTH: 12178
<212> TYPE: DNA
<213> ORGANISM: Homo sapiens

<400> SEQUENCE: 3
ggcccacaga ggagcacagc tgtgtttggc tgcagggcca agagcgctgt caagaagacc    60
cacacgcccc cctccagcag ctgaattcct gcagctcagc agccgccgcc agagcaggac   120
gaaccgccaa tcgcaaggca cctctgagaa cttcaggtag gagaaaagca aactccctcc   180
aacctcttac ttcgggctta aggcagagaa ctcgcctccc cagaatctcc tccctccatg   240
atcccccgct attcctctat tttctttttcc tcggacctgc agccttgggt cgaccctgcc   300
ctaggggtga ctgcaggaga gcagggagga tggtcaggcg tcaccaacaa cccatcacc    360 cagtaacaag aaccttgact ctctcagtcc ctctgcatca agacacttac ccatttccca   420
cctcatgcct gctaacttga atgaaacaat cgctgggaaa gcattaagag aattaaggct   480
```

-continued

| | |
|---|---|
| gggcactgtg gctcatgcct gtaatcccag cactttgtga ggctgaggca ggcagataac | 540 |
| ttgagcccag gagtttgaga ccagcctggg caacatggca aaaccctgct ctcccaaaaa | 600 |
| aatacaaaaa ttagctgggc gtgctggtgt gcctgtattc ccagctactt gggaggctga | 660 |
| ggtgggagga ttgcttcagc tggggaggcg gaggctgcag ggagccaaga ctgagccatt | 720 |
| gcacccagcc tgggtgacag agcaagaccc tgtctctaaa aatgaatgaa aggaaggaag | 780 |
| aaagagagag aaagagagag aggaaagaag gaaggaagta aagaagaaag aaagaaagaa | 840 |
| agaggaaaga ggaagaaaga aagaaaagaa agaaaagaaa gaaagcaaa tttaaagctt | 900 |
| atgcaaatca aagatgttgt gataattgat aattgagtct gggctaaatt ccccctgggc | 960 |
| tgcaaaggca gagagtggta atgacttctc acctgctttt cttctaaggc tttttacgg | 1020 |
| gacacagagg gaagggagat ggactggatt ccaagattcc cacagggcaa gatgggcgaa | 1080 |
| gactccctgc cactgcccgg ggataagtca gtctgagtga gacggagtgg gatgggctta | 1140 |
| gaacctgaac atgtcatggt ctcttcctgc accttgccct agtgttcact taccacctgc | 1200 |
| ttgcaggaaa caagaagagc agggcccaca gctggccagc tcccctcccc tcccgcctgt | 1260 |
| cttccagaac gattccttca ccagccctct ttccattgct ctaggatgca gatgtctcca | 1320 |
| gccctcacct gcctagtcct gggcctggcc cttgtctttg gtgaagggtc tgctgtgcac | 1380 |
| catcccccat cctacgtggc ccacctggcc tcagacttcg gggtgagggt gtttcagcag | 1440 |
| gtggcgcagg cctccaagga ccgcaacgtg gtttttctcac cctatggggt ggcctcggtg | 1500 |
| ttggccatgc tccagctgac aacaggagga gaaacccagc agcagattca agcagctatg | 1560 |
| ggattcaaga ttgatggtga gccacgggac accaggggag gtgggtggca tgcagaacag | 1620 |
| acctaccaga agccaaggaa aggctggctc tggcttagcc gagccaagcc ccatacagct | 1680 |
| gtgctgcagg ggccaccccca tcttcttccc actacactcc aagtcactgg acccttgaat | 1740 |
| ctccaagggt gtctgaccag tagatttacc gcttattcac caccgtgtga tcttaacctc | 1800 |
| gttaagtttg cccatctaca aaatgaggat tatttgctgt cctaaagaat tcatgagccg | 1860 |
| ggcgcggtgg ctcaaacgcc tgtaatccca gcactttggg aggccaaggc gggcggatca | 1920 |
| tgaggtcagg agatcaagac catcctggct aacacagtga aactccatct ctactaaaaa | 1980 |
| tacaaaaaaa attagccagg cgtggtggca ggcgcctgta gtcccagcta ctcgggaggc | 2040 |
| tgaggcagga gaatggcatg aacccaggag gcagagcttg cagtgagctg agatcgtgcc | 2100 |
| actgcactcc agcctgggcg acagagagag actccgtctc aaaaaaaaaa aataaaagaa | 2160 |
| ttcatggaat tacacttgtg aaatacttag catagccatc actataggaa aaaaatctaa | 2220 |
| ggccaggcac agtgcctcat gcctgtaatc tcagcacttt cggagtttga ggcaggagga | 2280 |
| tcacccaagg ctaggagttc aaggccagcc tgggcaatac ggtgaaaccc cgtctctaat | 2340 |
| aaaaatataa aaattagtct gatgaggtgg tgcacctgta atcccagcta ctcaggaagc | 2400 |
| tgagacacaa gaatcacttt aacccgggag gtggaggtgg cagtgagctg agatcacacc | 2460 |
| attgcactcc agcctgggtg acagagtgag acctgtcaaa aaaagaaaa gaaagagaga | 2520 |
| gagagagaga agagagagaa agaaagaaga agaaagaaag aaagagagag agagaaagaa | 2580 |
| agaaagaaac aaagaaacaa agaaagaaag gaaaagaaaa aaaaaactaa ggccaggcaa | 2640 |
| ggtggcttat gactgtaatt tcagcacttt ggaagattga ggcaggagga tcacttgagg | 2700 |
| ccagaagttc gagacaagac tgagcaacag ggagacccct gcctctacaa aaaaatttac | 2760 |
| aaattagcca gatgtggtga cacatacctg tagtcccaac tactcaggag ctgaggtgg | 2820 |
| gaggatggct tgagcccagg agctggaggc tgcagtgagc tatgattgta ccactgcact | 2880 |

```
tcagcctggg caacaaaggg aagccctgtc tgaaaaaaaa aaaaaaagaa aaagaagaag    2940
aaagaaaata tttagggttc atccaggagg cagaggttgc agtaagctga catcgcgcca    3000
ttgcactcca gcctgggaga caagagcaaa actccaactc aaaaaaaaaa aaaaaaaaaa    3060
aacaggaaga aaatatttag ggttcataat ttaagaacag agaaaaatat tctagcccaa    3120
agaaagggtt gggatctgag acttttgaag aaggaagga gatacagaaa agagatttca    3180
tcctggaatg aaatctccct ccagagagcc ctgggaaagc acggtagccc catccatca    3240 gagtggagcc ccttgtgggg gaagtgggct cggctgggaa ccctcaattc agcataagcc    3300
tcacatgtcc tctcctctct gtcccggtgc agacaagggc atggccccg ccctccggca    3360 tctgtacaag gagctcatgg ggccatggaa caaggatgag atcagcacca cagacgcgat    3420
cttcgtccag cgggatctga agctggtcca gggcttcatg ccccacttct tcaggctgtt    3480
ccggagcacg gtcaagcaag tggactttc agaggtggag agagccagat tcatcatcaa    3540
tgactgggtg aagacacaca caaaaggtga gcaggcaggg aaaggaaacc catttcctgg    3600
gcctcaagag aaagggaatt tggaaataaa tccacatatc ccagttgggt gcagtagttc    3660
acacctgtaa tcccagccca cactttggg aggtctaggc gagaggaagg cttgaggcct    3720
ggagtttgag accagcctgg ccaacataac aagacctcat ctcttcaaaa aatttaaaaa    3780
ccagccgggc atggtggtgc acacctgtag tcccagctac ttgggaggct gaggtgggag    3840
gatcacttga gtccagcagt tcaaggctgc agtgagctat gtttgcacca ccacactcca    3900
gcctgggtca cagaacaaga cctcatctct aaaaaacaaa caaaaaccaa atccacatat    3960
cctaaaaaat gctccttttc agcattctct tctctatgga caaagggctg gatgctttaa    4020
gaaccaaatc ttaggctggg cacggtggct cacgcctcta atcctagcac tttgagaggc    4080
caaggcgggc agattgcctg agcacaggag ttcgagacca gctggccaa catggtgaaa    4140 ccctgtctct gtcaaaaata caaaaaatta gccaggtgtg ttggcgcatg cctataatcc    4200
cagctgctcg ggaggatgag gttcaaagaa tcacttgaac ccgggaggca gaggctgcag    4260
tgagctgaga tcatgccact gcactccagc ctgggtgaca gagcaagact ttgtctccaa    4320
aaaaaggaac tagacgggtt catttaaacc cctgactgca gcccttttgac atacatccaa    4380 ttgaggactg gggactccgg gaaacatcta aaaggcttaa aaactttgtc taacttcagc    4440
cgggcatggt ggctcacacc tgtaatccca gcactttggg aggctaaggc aggtggatca    4500
aaaggtcagg agtttgagac gagcctgacc aacatggtga accccgtcct ctactaaaaa    4560
tacaaaaatt agccaggcat ggtggcaggc gcctgtaatc ccagctattc gggaggctga    4620
ggcaggagaa ttgcttgaac cccggagaca gaggttgcag cgagccgaga tcgcgccact    4680
gcactccagc ctggcaatag agtgagactc catctcaaaa caacaacaac aacaacaaca    4740
aaatcgtcta acttcctgat cttcctgatc attgattttc ccataggtat gatcagcaac    4800
ttgcttggga aggagccgt ggaccagctg acacggctgg tgctggtgaa tgccctctac    4860
ttcaacggcc agtggaagac tcccttcccc gactccagca cccaccgccg cctcttccac    4920
aaatcagacg gcagcactgt ctctgtgccc atgatggctc agaccaacaa gttcaactat    4980
agtaagtcca agagccccct ccccacagcc cacagcaact gcatctcatt cctggggtct    5040
cccaaggaat acccaaaatg tcaccctctg agggaggaag accacaggga atgctcccct    5100
ttaagggagg agagaccta gaatatactc cagctttgac aaagatttcc caagcaggag    5160
acatcaggat aatgggaaca gaagacagga ggtttatccc atgaaggatg aagaagctga    5220
```

```
aatccagaga ttccctcagg gccacatttg tccacctgac tccagggtct catcttcgtg   5280
tgttgctagt gtgattacct ggggatgaga aatcctgctg ggggagttga ggttaagagg   5340
atgaggactc caggtgctgt ggctcacgcc tgtaatccca gcactttggg aggccaaggc   5400
aggtggatca ggagtttgag gtcaggagtt tgagaccagc ctggccaaca tggtgaaacc   5460
ctgtctctac taaaaatgca aaaattagcc aggtgtggtg gcaggcgcct gtaatcccag   5520
ctactcggga ggctgaggca ggagaatcac ttgagcccgg gaggtggagg ttgcagtgag   5580
ccgaacgaaa ttgagccact tcaccccagc ctgggcaaaa gagtgaaatt ccattcaaaa   5640
aaaaaaaaaa aaaaaaagg atgaggactg ggatgaactg gtggctgggt gtggggaaaa    5700
tggaagtgaa ggaaggccaa aagagacaga gaaggcctgg cgcggcgact cacgcctata   5760
atcccagcac tttgggaggc tgagaagggg gattgcttga ggccagaagt tgaataccag   5820
tctgggcagc atagcaagac cctgcctcta caaaaaaaaa attttttttta attagccagg   5880 cttggtgaca tgcatctgta gtctactcaa gaagctgagg tgaggccagg cacggtggct   5940
cacgcctgta ttcccagcac tttgggaggt caaggcgggt ggatgacctg aggtcaggag   6000
ttcaagacca gcctggccaa catggtgaaa ccccatctgt ataaaaatac aaaaattagc   6060
tgggcatgat agcaggtgcc tgtaattcca gctactcagg aggctgaggt gggagaatct   6120
attgaacccg ggaggggggag gttgcagtga gccgagatca tgccattgca ctccagcctg   6180
ggcgacagag tgagactcct tctcaaaaca aacaaacaaa caaacaaaca aatacagaa    6240 gctgaggcgg gaggaacatt tgaaccggat tcggaggctg cagtgagcta tgattgcacc   6300
actgcgctcc agtctgtgtg acagtgagac cctgtctctt acacacacac acacacacac   6360
acacatgcac acacacagag agagagaaat tagaagatac tgaattggca gaagagaagg   6420
gaaatagaaa ttaaaatact gaataggga gcagtgaaca ggggatacc aaaagccaag     6480 agcgagagag agcctggctt ccagaaatag tggagaagcc aggagaacta ggtgaaaacc   6540
cagtgctggg ttgccatcag cgagagctgg agccatttcc aacgaaccat cttgtcgtct   6600
tcacagctga gttcaccacg cccgatggcc attactacga catcctggaa ctgccctacc   6660
acggggacac cctcagcatg ttcattgctg cccccttatga aaaagaggtg cctctctctg    6720
ccctcaccaa cattctgagt gcccagctca tcagccactg gaaaggcaac atgaccaggc   6780
tgccccgcct cctggttctg cccaagtaag ccaccccgct atctccccga cctaccaacc   6840
cctctctcct ggctccctaa agtcaccgcc cccaggttga atttcccaga tctgtgatgc   6900
ttgcaggaca tgcatgtgtg ggaggctgat gggaaactgt ggcctgggtt tgattatgag   6960
tcttgcaatc atccctcccc ctgtttctgc tggagggcag gggacagctc ttcctgacca   7020 caccccaca ttgactatcc ccagaatacc cagcaaaagc ccccaaaagg agagtcagag    7080
aaatgaggga ggtgggggcc caatcagtcc acatctactt agggtcgccc catcagcact   7140
tccatcccca accctttcaa gtcaacatcc aaacaaaaga aatcacttcc aaggacggag   7200
cagctcaaag cgcagcttct agctgggtt ccaagaaagc agatttttcg aaatccttct     7260
gcagaaggaa gcaaagagat tttttgaaat ctttctgcag aaggagaagg ctggagctgg   7320
ggaactccag aattataggg aagcctccca ccacgctcat cccaaatttc cggatgctat   7380
aatgccaggc ttggggaaag aggagaattt agttggttag ctggtgcgtg ctctcacttg   7440
catcctctct cttcctctttt ttttttttc tcctctctct ctggctcata aaaatggagg    7500
taattagttg tgccctggtg agaagcagag agtgcacaaa ggcccctgc ttgagtcctc     7560 ttcagggtta gctctcagaa acacaatctg cagaacagat ttttgttcca acatccttgc   7620
```

```
aggagaattt gcccttagct tcccccaccc cagccaggct gaataaaatt atgctgaaac   7680
tactgtctta tttgaggaaa gtaattagtc ataggtggga gggggtgggg agattgcaga   7740
agaatgttca tgaatattag gattttcagc tctaaggggg gactttgtaa acagctttag   7800
aagaagaacc aggccggctg ggtgtggtgg ctcatgcctg taatctcagc atttggggag   7860
gccaaggcgg gcggatcact tgaggtcagg agtttgagac cagcctggcc aacatggtga   7920
aaccctgtct ctattaaaaa tacaaaaatt agccagccgt ggtagcgagc gcctatgatc   7980
ccagctactc cggaggctga ggccagagaa tcacatgaac ctgggaggtg gaggctgcag   8040
tgagccgaga tcacgccact gcactccagc ctggggaca gagcaagaat ctgtttcaaa    8100 aaaaaaaaa gaaaatagg aaggaaggaa ggaaggaaa ggaagaaga gagagagaaa       8160 gaaagagaga gagagaaaga aagaaagaaa gaaagaaaga aagaaagaaa gaaagaaaga   8220
aagaaagaaa gaaagaaaaa gaaaggaaag aaagaacgaa cgaaccaggc ctccctctcc   8280
aaccttcacc tccgtcccta ttctggccac ttgattcggg ggacacctgg taggggatgg   8340
ggaaaggtgg gagctgccag ccagagggga ccccggcttg agcagcctct tgctgctatc   8400
tgcaggttct ccctggagac tgaagtcgac ctcaggaagc ccctagagaa cctgggaatg   8460
accgacatgt tcagacagtt tcaggctgac ttcacgagtc tttcaggtaa gaagactttc   8520 cttttgcattt tctcacccca gtggactgcg ggggccccta agaggaaaaa ggaacctctc   8580
cttgagagcg gcagctgatc taatcctgta tccacatctg tttcagacca agagcctctc   8640
cacgtcgcgc aggcgctgca gaaagtgaag atcgaggtga acgagagtgg cacggtggcc   8700
tcctcatcca caggtgagtc tggctcaggt gaggctccac gggtgtcgcc tccatcgccc   8760
ttcaggataa ctggtcccca gacccggaaa ggaccccgca gccctctcgg cacagagcag   8820
ctctgtctgt gctcagccat cacccactcc ccacctgttt ctcagcctgg aaaacgggct   8880
tgggaccatg gaaccctgtt tcctcgcctg atggctccta agttccctga ctgtgaaaag   8940
gcctcctaaa gaaaaaccca agttgttccc acagtgggaa gtaaacttaa gaaacatgct   9000
tatcaggctg ggcatggtgg ctcccacctg taatcccagc gctttggggg accaaggcag   9060
gtggatcact tgaggtcagg aattcgagac cagcctgggc aacatggcaa accctatct   9120 ctactaaaaa tacaaaaatt aggcaggcgt ggtggcatgt gcctgtagtc ccagctactt   9180
gggaggctga ggcaggagaa tcacttgaat ccaggaggca gaggttgcag tgagccgaga   9240
tcacgctgct gcactccagc ctgggcaata gagcatgact ctgaagaaaa gaaagaaaga   9300 agagagaga gagagaaaag aaagaaagaa agaaagaaag aaagaaagaa agaaagaaag    9360
aaagaaagaa agaaagagaa agaaagagaa gaaagagaaa gaaagagctt atcaataagc   9420
ccttaaagga tttagataaa tgtgtgtaag ggaagagctg atccattgct accaagctcc   9480
tggaggaaac caggtctcag aggatgtccc taaacttttta aggttcatat tcaggaaaac   9540
aaacaacttc cagctgggct tagtggctca cacctgtaat cccagcactt tgggaggccg   9600
aggcaggagg atcgcttgag cccaggaatt tgagaccagc ctgggcaata taatgagact   9660
gtgtctctac aaaaattaga aaaaaattag ccaggcatgg tggcatgcac ctgtagcccc   9720
agttacttgg gagactgagg tgggaggatc acttgagccc atgagttcaa ggctgcagtg   9780
agccatgaag gtgccactgc actcccacct gggcgacaga gggagaccct gtctctaaga   9840
aaaacggcgg gggtggggt ggtgccagtg ccagcatccc tctgttctaa gacattgtcc    9900
cttctcttgc agctgtcata gtctcagccc gcatggcccc cgaggagatc atcatggaca   9960
```

```
gacccttcct ctttgtggtc cggcacaacc ccacaggtga gcctggaacc catcacgttc    10020
cacatcctcc cacccattct ttctctcagg aactagtccc gacagatgca gacatccctc    10080
tatccctgag agggctctgg gcagggaacc cataaccta ccctgcttcc tgtcccaaga     10140
ggaggctacc ttctatcacc cacagacagt gccgggtccc cgctctgtga ctcaggcagc    10200
tgcgactcca gacagctcac tcatctgcct agatctcagt ccttccaccc acatccagcc    10260
tgatgagctg tcccactcct tctgcttctc aaccccatg gttcttccac cctcaggaac     10320 agtcctttc atgggccaag tgatggaacc ctgaccctgg ggaagacgc cttcatctgg      10380 gacaaaactg gagatgcatc gggaagaag aaactccgaa gaaagaatt ttagtgttaa      10440 tgactctttc tgaaggaaga gaagacattt gccttttgtt aaaagatggt aaaccagatc    10500
tgtctccaag accttggcct ctccttggag gaccttagg tcaaactccc tagtctccac     10560
ctgagaccct gggagagaag tttgaagcac aactccctta aggtctccaa accagacggt    10620
gacgcctgcg ggaccatctg gggcacctgc ttccacccgt ctctctgccc actcgggtct    10680
gcagacctgg ttcccactga ggcccttgc aggatggaac tacggggctt acaggagctt     10740
ttgtgtgcct ggtagaaact atttctgttc cagtcacatt gccatcactc ttgtactgcc    10800
tgccaccgcg gaggaggctg gtgacaggcc aaaggccagt ggaagaaaca cccttcatc     10860 tcagagtcca ctgtggcact ggccacccct ccccagtaca ggggtgctgc aggtggcaga    10920
gtgaatgtcc cccatcatgt ggcccaactc tcctggcctg gccatctccc tccccagaaa   10980
cagtgtgcat gggttatttt ggagtgtagg tgacttgttt actcattgaa gcagatttct    11040
gcttcctttt atttttatag gaatagagga agaaatgtca gatgcgtgcc cagctcttca    11100
ccccccaatc tcttggtggg gaggggtgta cctaaatatt tatcatatcc ttgcccttga    11160
gtgcttgtta gagagaaaga gaactactaa ggaaaataat attatttaaa ctcgctccta    11220
gtgtttcttt gtggtctgtg tcaccgtatc tcaggaagtc cagccacttg actggcacac    11280 accccctccgg acatccagcg tgacggagcc cacactgcca ccttgtggcc gcctgagacc    11340
ctcgcgcccc ccgcgcccct cttttccc ttgatggaaa ttgaccatac aatttcatcc       11400
tccttcaggg gatcaaaagg acggagtggg gggacagaga ctcagatgag gacagagtgg    11460
tttccaatgt gttcaataga tttaggagca gaaatgcaag gggctgcatg acctaccagg    11520
acagaacttt ccccaattac agggtgactc acagccgcat tggtgactca cttcaatgtg    11580
tcatttccgg ctgctgtgtg tgagcagtgg acacgtgagg gggggtggg tgagagagac     11640 aggcagctcg gattcaacta ccttagataa tatttctgaa aacctaccag ccagagggta    11700
gggcacaaag atggatgtaa tgcactttgg gaggccaagg cgggaggatt gcttgagccc    11760
aggagttcaa gaccagcctg gcaacatac caagacccccc gtctctttaa aaatatatat    11820
attttaaata tacttaaata tatatttcta atatctttaa atatatatat atattttaaa    11880
gaccaattta tgggagaatt gcacacagat gtgaaatgaa tgtaatctaa tagaagccta    11940
atcagcccac catgttctcc actgaaaaat cctctttctt tggggttttt ctttctttct    12000
tttttgattt tgcactggac ggtgacgtca gccatgtaca ggatccacag gggtggtgtc    12060
aaatgctatt gaaattgtgt tgaattgtat gcttttcac ttttgataaa taaacatgta     12120
aaaatgtttc aaaaaaataa taaaataaat aaatacgaag aatatgtcag gacagtca      12178
```

<210> SEQ ID NO 4
<211> LENGTH: 22
<212> TYPE: DNA
<213> ORGANISM: artificial

```
<220> FEATURE:
<223> OTHER INFORMATION: Oligonucleotide base sequence

<400> SEQUENCE: 4
cccctctggt caaccagtca ca                                              22

<210> SEQ ID NO 5
<211> LENGTH: 19
<212> TYPE: DNA
<213> ORGANISM: Artficial

<400> SEQUENCE: 5
cctctggtca accagtcac                                                  19

<210> SEQ ID NO 6
<211> LENGTH: 15
<212> TYPE: DNA
<213> ORGANISM: Artificial
<220> FEATURE:
<223> OTHER INFORMATION: Oligonucleotide base sequence

<400> SEQUENCE: 6
tggtcaacca gtcac                                                      15

<210> SEQ ID NO 7
<211> LENGTH: 402
<212> TYPE: PRT
<213> ORGANISM: Homo sapiens

<400> SEQUENCE: 7
```

Met Gln Met Ser Pro Ala Leu Thr Cys Leu Val Leu Gly Leu Ala Leu
1               5                   10                  15

Val Phe Gly Glu Gly Ser Ala Val His His Pro Ser Tyr Val Ala
            20                  25                  30

His Leu Ala Ser Asp Phe Gly Val Arg Val Phe Gln Gln Val Ala Gln
        35                  40                  45

Ala Ser Lys Asp Arg Asn Val Val Phe Ser Pro Tyr Gly Val Ala Ser
    50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
            100                 105                 110

Glu Ile Ser Thr Thr Asp Ala Ile Phe Val Gln Arg Asp Leu Lys Leu
        115                 120                 125

Val Gln Gly Phe Met Pro His Phe Phe Arg Leu Phe Arg Ser Thr Val
    130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
            180                 185                 190

Tyr Phe Asn Gly Gln Trp Lys Thr Pro Phe Pro Asp Ser Ser Thr His
        195                 200                 205

Arg Arg Leu Phe His Lys Ser Asp Gly Ser Thr Val Ser Val Pro Met
    210                 215                 220

```
Met Ala Gln Thr Asn Lys Phe Asn Tyr Thr Glu Phe Thr Thr Pro Asp
225                 230                 235                 240

Gly His Tyr Tyr Asp Ile Leu Glu Leu Pro Tyr His Gly Asp Thr Leu
            245                 250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Val Leu Pro Lys Phe Ser Leu Glu
        290                 295                 300

Thr Glu Val Asp Leu Arg Lys Pro Leu Glu Asn Leu Gly Met Thr Asp
305                 310                 315                 320

Met Phe Arg Gln Phe Gln Ala Asp Phe Thr Ser Leu Ser Asp Gln Glu
            325                 330                 335

Pro Leu His Val Ala Gln Ala Leu Gln Lys Val Lys Ile Glu Val Asn
            340                 345                 350

Glu Ser Gly Thr Val Ala Ser Ser Thr Ala Val Ile Val Ser Ala
        355                 360                 365

Arg Met Ala Pro Glu Glu Ile Ile Met Asp Arg Pro Phe Leu Phe Val
        370                 375                 380

Val Arg His Asn Pro Thr Gly Thr Val Leu Phe Met Gly Gln Val Met
385                 390                 395                 400

Glu Pro

<210> SEQ ID NO 8
<211> LENGTH: 15
<212> TYPE: DNA
<213> ORGANISM: Artificial
<220> FEATURE:
<223> OTHER INFORMATION: Oligonucleotide base sequence

<400> SEQUENCE: 8
tggtcaacca gtcac                                                    15

<210> SEQ ID NO 9
<211> LENGTH: 71
<212> TYPE: RNA
<213> ORGANISM: Mus musculus

<400> SEQUENCE: 9
agggugugug acugguugac cagaggggcg ugcacucugu ucacccugug ggccaccuag    60
ucaccaaccc u                                                        71

<210> SEQ ID NO 10
<211> LENGTH: 25
<212> TYPE: RNA
<213> ORGANISM: Mus musculus

<400> SEQUENCE: 10
aaaaucguuu guguuccagu cacac                                         25
```